US005854053A

United States Patent [19]
Donovan et al.

[11] Patent Number: 5,854,053
[45] Date of Patent: Dec. 29, 1998

[54] BACILLUS THURINGIENSIS BACTERIA

[75] Inventors: William P. Donovan, Levittown, Pa.; José M. González, Jr., Trenton, N.J.

[73] Assignee: Ecogen, Inc., Langhorne, Pa.

[21] Appl. No.: 779,046

[22] Filed: Jan. 6, 1997

Related U.S. Application Data

[62] Division of Ser. No. 474,038, Jun. 7, 1995, Pat. No. 5,679,343, which is a division of Ser. No. 176,865, Dec. 30, 1993, Pat. No. 5,616,319, which is a division of Ser. No. 100,709, Jul. 29, 1993, Pat. No. 5,322,687.

[51] Int. Cl.$^6$ .............................. C12N 1/20; A01N 63/00
[52] U.S. Cl. .................. 435/252.5; 435/832; 424/93.461
[58] Field of Search ................................ 435/252.5, 832; 424/93.461

[56] References Cited

U.S. PATENT DOCUMENTS

| | | | |
|---|---|---|---|
| 5,080,897 | 1/1992 | Gonzalez, Jr. et al. | 424/93 |
| 5,204,237 | 4/1993 | Gaertner et al. | 435/6 |
| 5,441,884 | 8/1995 | Baum | 435/252.31 |

FOREIGN PATENT DOCUMENTS

| | | |
|---|---|---|
| 289479 | 11/1988 | European Pat. Off. . |
| 295156 | 12/1988 | European Pat. Off. . |
| 358557 | 3/1990 | European Pat. Off. . |
| 367474 | 5/1990 | European Pat. Off. . |
| 401979 | 12/1990 | European Pat. Off. . |
| 405810 | 1/1991 | European Pat. Off. . |
| 462721 | 12/1991 | European Pat. Off. . |
| 90/13651 | 11/1990 | WIPO . |
| 91/16434 | 10/1991 | WIPO . |

OTHER PUBLICATIONS

Gleave et al., "Identification of An Insecticidal Crystal Protein from *Bacillus thuringiensis* DSIR517 with Significant Sequence Differences from Previously Described Toxins," *J. Gen. Microbiol.*, 138:55–62 (1992).

Turner et al., "Stability of the δ–Endotoxin Gene from *Bacillus thuringiensis* subsp. *kurstaki* in a Recombinant Strain of *Clavibacter xyli* subsp. *cynodontis*," *Appl. Environ. Microbiology.*, 57:3522–3528 (1991).

Smulevitch et al., "Nucleotide Sequence of a Novel δ–Endotoxin Gene *cryIg* of *Bacillus thuringiensis* ssp. *galleriae*," *FEBS Lett.*, 293:25–28 (1991).

Chambers et al., "Isolation and Characterization of a Novel Insecticidal Crystal Protein Gene from *Bacillus thuringiensis* subsp. *aizawai*," *J. Bacteriol.*, 173:3966–3976 (1991).

Perlak et al., "Modification of the Coding Sequence Enhances Plant Expression of Insect Control Protein Genes," *Proc. Natl. Acad. Sci. USA*, 88:3324–3328 (1991).

Macaluso et al., "Efficient Transformation of *Bacillus thuringiensis* Requires Nonmethylated Plasmid DNA," *J. Bacteriol.*, 173:1353–1356 (1991).

Von Tersch et al., "Insecticidal Toxins from *Bacillus thuringiensis* subsp. *kenyae*: Gene Cloning and Characterization and Comparison with *B. thuringiensis* subsp. *kurstaki* CryIA(c) Toxins," *Appl. Environ. Microbiology*, 57:349–358 (1991).

Visser et al., "A Novel *Bacillus thuringiensis* Gene Encoding a *Spodoptera exigua*–specific Crystal Protein," *J. Bacteriol.*, 172:6783–6788 (1990).

Mettus et al., "Expression of *Bacillus thuringiensis* δ–Endotoxin Genes During Vegetative Growth," *Appl. Environ. Microbiology*, 56:1128–1134 (1990).

Hodgman et al., "Models for the Structure and Function of the *Bacillus thuringiensis* δ–Endotoxins Determined by Compilational Analysis," *J. DNA Sequencing and Mapping*, 1:97–106 (1990).

Höfte et al., "Insecticidal Crystal Proteins of *Bacillus thuringiensis*," *Microbiol. Rev.*, 53:242–255 (1989).

Sanchis et al., "Nucleotide Sequence and Analysis of the N–terminal Coding Region of the Spodoptera–active δ–Endotoxin Gene of *Bacillus thuringiensis aizawai* 7.29," *Molecular Microbiol.*, 3:229–238 (1989).

Masson et al., "Nucleotide Sequence of a Gene Cloned from *Bacillus thuringiensis* subspecies *entomocidus* Coding for an Insecticidal Protein Toxic for *Bombyx mori*," *Nucl. Acids Res.*, 17:446 (1989).

Haider et al., "Nucleotide Sequence of a *Bacillus thuringiensis aizawai* IC1 Entomocidal Crystal Protein Gene," *Nucl. Acids Res.*, 16:10927 (1988).

Honée et al., "Nucleotide Sequence of Crystal Protein Gene Isolated from *B. thuringiensis* subspecies *entomocidus* 60.5 Coding for a Toxin Highly Active Against *Spodoptera* species," *Nucl. Acids. Res.*, 16:6240 (1988).

Brizzard et al., "Nucleotide Sequence of an Additional Crystal Protein Gene Cloned from *Bacillus thuringiensis*," *Nucl. Acids. Res.*, 16:2723–2724 (1988).

Shimizu et al., "Cloning and Expression in *Escherichia coli* of the 135–kDa Insecticidal Protein Gene from *Bacillus thuringiensis* subsp. *aizawai* IPL7," *Agric. Biol. Chem.*, 52:1565–1573 (1988).

Visser et al., "Genes from *Bacillus thuringiensis entomocidus* 60.5 Coding for Insect–specific Crystal Proteins," *Mol. Gen. Genet.*, 212:219–224 (1988).

Fischoff et al., "Insect Tolerant Transgenic Tomato Plants," *Bio/Technology*, 5:807–813 (1987).

(List continued on next page.)

*Primary Examiner*—Rebecca E. Prouty
*Attorney, Agent, or Firm*—Panitch Schwarze Jacobs & Nadel, P. C.

[57] ABSTRACT

A *Bacillus thuringiensis* strain isolate, designated *B.t.* strain EG5847, exhibits insecticidal activity against lepidopteran insects. Two novel toxin genes from *B.t.* strain EG5847 designated cryET4 and cryET5 produce insecticidal proteins with activity against a broad spectrum of insects of the order Lepidoptera. The cryET4 gene has a nucleotide base sequence shown in FIG. 1 and listed in SEQ ID NO:1 and produces a CryET4 gene product having the deduced amino acid sequence shown in FIG. 1 and listed in SEQ ID NO:2. The cryET5 gene has a nucleotide base sequence shown in FIG. 2 and listed in SEQ ID NO:3 and produces a CryET5 gene product having the deduced amino acid sequence shown in FIG. 2 and listed in SEQ ID NO:4.

2 Claims, 25 Drawing Sheets

OTHER PUBLICATIONS

Oeda et al., "Nucleotide Sequence of the Insecticidal Protein Gene of *Bacillus thuringiensis* Strain *aizawai* IPL7 and its High–level Expression in *Escherichia coli*," *Gene*, 53:113–119 (1987).

Hefford et al., "Sequence of a Lepidopteran Toxin Gene of *Bacillus thuringiensis* subsp. *kurstaki* NRD–12," *J. Biotechnology*, 6:307–322 (1987).

Kondo et al., "Cloning and Nucleotide Sequencing of Two Insecticidal δ–Endotoxin Genes from *Bacillus thuringiensis* var. *kurstaki* HD–1 DNA," *Agric. Biol. Chem.*, 51:455–463 (1987).

Geiser et al., "The Hypervariable Region in the Genes Coding for Entomopathogenic Crystal Proteins of *Bacillus thuringiensis*: Nucleotide Sequence of the *kurhdl* gene of subsp. *kurstaki* HD1," *Gene*, 48:109–118 (1986).

Obukowicz et al., "Integration of the Delta–endotoxin Gene of *Bacillus thuringiensis* Into the Chromosome of Root–colonizing Strains of Pseudomonads Using Tn5," *Gene*, 45:327–331 (1986).

Wabiko et al., "*Bacillus thuringiensis* Entomocidal Protoxin Gene Sequence and Gene Product Analysis," *DNA*, 5:305–314 (1986).

Höfte et al., "Structual and Functional Analysis of a Cloned Delta Endotoxin of *Bacillus thuringiensis berliner* 1715," *Eur. J. Biochem.*, 161:273–280 (1986).

Schnepf et al., "The Amino Acid Sequence of a Crystal Protein from *Bacillus thuringiensis* Deduced from the DNA Base Sequence," *J. Biol. Chem.*, 260:6264–6272 (1985).

Adang et al., "Characterized Full–length and Truncated Plasmid Clones of the Crystal Protein of *Bacillus thuringiensis* subsp. *kurstaki* HD–73 and Their Toxicity to *Manduca sexta*," *Gene*, 36:289–300 (1985).

Shibano et al., "Nucleotide Sequence Coding for the Insecticidal Fragment of the *Bacillus thuringiensis* Crystal Protein," *Gene*, 34:243–251 (1985).

Carlton et al., "Plasmids and Delta–Endotoxin Production in Different Subspecies of *Bacillus thuringiensis*," *Molecular Biology of Microbial Differentiation*, pp. 246–252, J.A. Hoch and P. Setlow, ed., American Society for Microbiology, Washington, DC (1985).

King et al., "*Heliothis Virescens*," in *Handbook of Insect Rearing*, vol. II, pp. 323–328, P. Singh and R.F. Moore (eds.), Elsevier Science, Amsterdam (1985).

Kaiser et al., "Amphiphilic Secondary Structure: Design of Peptide Hormones," *Science*, 223:249–255 (1984).

Gonzalez, Jr., et al., "Transfer of *Bacillus thuringiensis* Plasmids Coding for δ–endotoxin Among Strains of *B. thuringiensis* and *B. cereus*," *Proc. Natl. Acad. Sci. USA*, 79:6951–6955 (1982).

FIGURE 1A

```
AAATTCATAA TATGAATCAT ACGTTTAAA ACGTTTTAAA GTGTTGTGAA GAAAAGAGAA TTGATCTTTA    60

GAATTTTTT ATTTAACCA AAGAGAAAGG GTAACTT ATG GAG ATA AAT AAT                    113
                                        Met Glu Ile Asn Asn
                                         1               5

CAG AAG CAA TGC ATA CCA TAT AAT TGC TTA AGT AAT CCT GAG GAA GTA               161
Gln Lys Gln Cys Ile Pro Tyr Asn Cys Leu Ser Asn Pro Glu Glu Val
             10                  15                  20

CTT TTG GAT GGG GAG AGG ATA TTA CCT GAT ATC GAT CCA CTC GAA GTT               209
Leu Leu Asp Gly Glu Arg Ile Leu Pro Asp Ile Asp Pro Leu Glu Val
        25                  30                  35

TCT TTG TCG CTT TTG CAA TTT CTT TTG AAT AAC TTT GTT CCA GGG GGA               257
Ser Leu Ser Leu Leu Gln Phe Leu Leu Asn Asn Phe Val Pro Gly Gly
                40                  45                  50

GGC TTT ATT TCA GGA TTA GTT GAT AAA ATA TGG GGG GCT TTG AGA CCA               305
Gly Phe Ile Ser Gly Leu Val Asp Lys Ile Trp Gly Ala Leu Arg Pro
    55                  60                  65

TCT GAA TGG GAC TTA TTT CTT GCA CAG ATT GAA CGG TTG ATT GAT CAA               353
Ser Glu Trp Asp Leu Phe Leu Ala Gln Ile Glu Arg Leu Ile Asp Gln
70                  75                  80                  85

AGA ATA GAA GCA ACA GTA AGA GCA AAA GCA ATC ACT GAA TTA GAA GGA               401
Arg Ile Glu Ala Thr Val Arg Ala Lys Ala Ile Thr Glu Leu Glu Gly
        90                  95                 100

TTA GGG AGA AAT TAT CAA ATA TAC GCT GAA GCA TTT AAA GAA TGG GAA               449
Leu Gly Arg Asn Tyr Gln Ile Tyr Ala Glu Ala Phe Lys Glu Trp Glu
            105                 110                 115
```

FIGURE 1B

```
TCA GAT CCT GAT AAC GAA GCG GCT AAA AGT AGA GTA ATT GAT CGC TTT    497
Ser Asp Pro Asp Asn Glu Ala Ala Lys Ser Arg Val Ile Asp Arg Phe
            120                 125                 130

CGT ATA CTT GAT GGT CTA ATT GAA GCA AAT ATC CCT TCA TTT CGG ATA    545
Arg Ile Leu Asp Gly Leu Ile Glu Ala Asn Ile Pro Ser Phe Arg Ile
            135                 140                 145

ATT GGA TTT GAA GTG CCA CTT TTA TCG GTT CAA TAT GTT CAA GCA GCT AAT    593
Ile Gly Phe Glu Val Pro Leu Leu Ser Val Gln Tyr Val Gln Ala Ala Asn
            150                 155                 160                 165

CTA CAT CTC GCT CTA TTG AGA GAT TCT GTT ATT TTT GGA GAG AGA TGG    641
Leu His Leu Ala Leu Leu Arg Asp Ser Val Ile Phe Gly Glu Arg Trp
            170                 175                 180

GGA TTG ACG ACA AAA AAT GTC AAT GAT ATC TAT AAT AGA CAA ATT AGA    689
Gly Leu Thr Thr Lys Asn Val Asn Asp Ile Tyr Asn Arg Gln Ile Arg
            185                 190                 195

GAA ATT CAT GAA TAT AGC AAT CAT TGC GTA GAT ACG TAT TAC AAC ACA GAA    737
Glu Ile His Glu Tyr Ser Asn His Cys Val Asp Thr Tyr Tyr Asn Thr Glu
            200                 205                 210

CTA GAA CGT CTA GGG TTT AGA TCT ATA GCG CAG TGG AGA ATA TAT AAT    785
Leu Glu Arg Leu Gly Phe Arg Ser Ile Ala Gln Trp Arg Ile Tyr Asn
            215                 220                 225

CAG TTT AGA AGA GAA CTA ACA CTA ACT GTA TTA GAT ATT GTC GCT CTT    833
Gln Phe Arg Arg Glu Leu Thr Leu Thr Val Leu Asp Ile Val Ala Leu
            230                 235                 240                 245
```

FIGURE 1C

```
TTC CCG AAC TAT GAC AGT AGA CTG TAT CCG ATC CAA ACT TTT TCT CAA    881
Phe Pro Asn Tyr Asp Ser Arg Leu Tyr Pro Ile Gln Thr Phe Ser Gln
            250                     255                 260

TTG ACA AGA GAA ATT GTT ACA TCC CCA GTA AGC GAA TTT TAT TAT GGT    929
Leu Thr Arg Glu Ile Val Thr Ser Pro Val Ser Glu Phe Tyr Tyr Gly
            265                     270                 275

GTT ATT AAT AGT GGT AAT ATA ATT GGT ACT CTT ACT GAA CAG CAG ATA    977
Val Ile Asn Ser Gly Asn Ile Ile Gly Thr Leu Thr Glu Gln Gln Ile
            280                     285                 290

AGG CGA CCA CAT CTT ATG GAC TTC TTT AAC TCC ATG ATC ATG TAT ACA   1025
Arg Arg Pro His Leu Met Asp Phe Phe Asn Ser Met Ile Met Tyr Thr
            295                     300                 305

TCA GAT AAT AGA CGG GAA CAT TAT TGG TCA GGA CTT GAA ATG ACG GCT   1073
Ser Asp Asn Arg Arg Glu His Tyr Trp Ser Gly Leu Glu Met Thr Ala
            310                     315                 320                 325

TAT TTT ACA GGA TTT GCA GGA GCT CAA GTG TCA TTC CCT TTA GTC GGG   1121
Tyr Phe Thr Gly Phe Ala Gly Ala Gln Val Ser Phe Pro Leu Val Gly
            330                     335                 340

ACT AGG GAG GAG TCA GCT CCA CCA TTA ACT GTT AGA AGT GTT AAT GAT   1169
Thr Arg Gly Glu Ser Ala Pro Pro Leu Thr Val Arg Ser Val Asn Asp
            345                     350                 355

GGA ATT TAT AGA ATA TTA TCG GCA CCG TTT TAT TCA GCG CCT TTT CTA   1217
Gly Ile Tyr Arg Ile Leu Ser Ala Pro Phe Tyr Ser Ala Pro Phe Leu
            360                     365                 370
```

FIGURE 1D

```
GGC ACC ATT GTA TTG GGA AGT CGT GGA GAA AAA TTT GAT TTT GCG CTT   1265
Gly Thr Ile Val Leu Gly Ser Arg Gly Glu Lys Phe Asp Phe Ala Leu
375                 380                 385

AAT AAT ATT TCA CCT CCG CCA TCT ACA ATA TAC ATA CAT CCT GGA ACA   1313
Asn Asn Ile Ser Pro Pro Pro Ser Thr Ile Tyr Ile His Pro Gly Thr
        390                 395                 400                 405

GTA GAT TCA CTA GTC AGT ATA CCG CCA CAG GAT AAT AGC GTA CCA CCG   1361
Val Asp Ser Leu Val Ser Ile Pro Pro Gln Asp Asn Ser Val Pro Pro
                410                 415                 420

CAC AGG GGA TCT AGT CAT CGA TTA AGT CAT GTT ACA ATG CGC GCA AGT   1409
His Arg Gly Ser Ser His Arg Leu Ser His Val Thr Met Arg Ala Ser
        425                 430                 435

TCC CCT ATA TTC CAT TGG ACG CAT CGC AGC GCA ACC ACT ACA AAT ACA   1457
Ser Pro Ile Phe His Trp Thr His Arg Ser Ala Thr Thr Thr Asn Thr
                440                 445                 450

ATT AAT CCA AAT GCT ATT ATC CAA ATA CCA CTA GTA AAA GCA TTT AAC   1505
Ile Asn Pro Asn Ala Ile Ile Gln Ile Pro Leu Val Lys Ala Phe Asn
        455                 460                 465

CTT CAT TCA GGT GCC ACT GTT AGA GGA CCA GGG TTT ACA GGT GGT       1553
Leu His Ser Gly Ala Thr Val Arg Gly Pro Gly Phe Thr Gly Gly
470                 475                 480                 485

GAT ATC CTT CGA AGA ACG AAT ACT GGC ACA TTT GCA GAT ATG AGA GTA   1601
Asp Ile Leu Arg Arg Thr Asn Thr Gly Thr Phe Ala Asp Met Arg Val
        490                 495                 500
```

FIGURE 1E

```
AAT ATT ACT GGG CCA TTA TCC CAA AGA TAT CGT GTA AGA ATT CGC TAT    1649
Asn Ile Thr Gly Pro Leu Ser Gln Arg Tyr Arg Val Arg Ile Arg Tyr
                505                 510                 515

GCT TCT ACG ACA GAT TTA CAA TTT TTC ACG AGA ATC AAT GGA ACT TCT    1697
Ala Ser Thr Thr Asp Leu Gln Phe Phe Thr Arg Ile Asn Gly Thr Ser
            520                 525                 530

GTA AAT CAA GGT AAT TTC CAA AGA ACT ATG AAT AGA GGG GAT AAT TTA    1745
Val Asn Gln Gly Asn Phe Gln Arg Thr Met Asn Arg Gly Asp Asn Leu
        535                 540                 545

GAA TCT GGA AAC TTT AGG ACT GCA GGA TTT AGT ACG CCT TTT AGT TTT    1793
Glu Ser Gly Asn Phe Arg Thr Ala Gly Phe Ser Thr Pro Phe Ser Phe
550                 555                 560                 565

TCA AAT GCG CAA AGT ACA TTC ACA TTG GGT ACT CAG GCT TTT TCA AAT    1841
Ser Asn Ala Gln Ser Thr Phe Thr Leu Gly Thr Gln Ala Phe Ser Asn
            570                 575                 580

CAG GAA GTT TAT ATA GAT CGA ATT GAA TTT GTC CCG GCA GAA GTA ACA    1889
Gln Glu Val Tyr Ile Asp Arg Ile Glu Phe Val Pro Ala Glu Val Thr
        585                 590                 595

TTC GAG GCA GAA TCT GAT TTA GAA CTA GGG AGA GCG CAA AAG GCG GTG AAT GCC    1937
Phe Glu Ala Glu Ser Asp Leu Glu Leu Gly Arg Ala Gln Lys Ala Val Asn Ala
600                 605                 610

CTG TTT ACT TCT ACA AAC CAA CTA GGG CTA AAA ACA GAT GTG ACG GAT    1985
Leu Phe Thr Ser Thr Asn Gln Leu Gly Leu Lys Thr Asp Val Thr Asp
615                 620                 625
```

FIGURE 1F

```
TAT CAG ATT GAT CAA GTG TCC AAT TTA GTA GAA TGT TTA TCA GAT GAA        2033
Tyr Gln Ile Asp Gln Val Ser Asn Leu Val Glu Cys Leu Ser Asp Glu
630                 635                 640                 645

TTT TGT CTG GAT GAA AAG AGA GAA TTG TCC GAG AAA GTC AAA CAT GCA        2081
Phe Cys Leu Asp Glu Lys Arg Glu Leu Ser Glu Lys Val Lys His Ala
            650                 655                 660

AAG CGA CTT AGT GAT AAG CGG AAC CTA CTT CAA GAT CCA AAC TTC ACA        2129
Lys Arg Leu Ser Asp Lys Arg Asn Leu Leu Gln Asp Pro Asn Phe Thr
        665                 670                 675

TCT ATC AAT AGA CAA CTA GAC CGT GGA TGG AGA GGA AGT GGG TAT ATT       2177
Ser Ile Asn Arg Gln Leu Asp Arg Gly Trp Arg Gly Ser Gly Tyr Asp Ile
    680                 685                 690

ACC ATC CAA GGA GGA AAT GAC TGT TAT CCA ACG TAT CAA AAA ATA CTA       2225
Thr Ile Gln Gly Gly Asn Asp Cys Tyr Pro Thr Tyr Gln Lys Ile Thr Leu
695                 700                 705                 725

CCA GGT ACC TTT GAT GAG CTT TAT ACT CGC TAT GAA TTA AGA GGG TAT       2273
Pro Gly Thr Phe Asp Glu Leu Tyr Thr Arg Tyr Glu Leu Arg Gly Tyr
710                 715                 720                 740

GAT GAG TCA AAA TTA AAA GCC TAT ACT CGC TAT GAA TTA AGA GGG TAT       2321
Asp Glu Ser Lys Leu Lys Ala Tyr Thr Arg Tyr Glu Leu Arg Gly Tyr
            730                 735                 740

ATT GAA GAT AGT CAA GAT TTA GAA GTC TAT TTG ATT CGT TAC AAT GCG       2369
Ile Glu Asp Ser Gln Asp Leu Glu Val Tyr Leu Ile Arg Tyr Asn Ala
        745                 750                 755
```

FIGURE 1G

```
AAA CAT GAA ACA GTA AAT CCC GGT ACA GGG TCC TTA TGG CCG CTT      2417
Lys His Glu Thr Val Asn Pro Gly Thr Gly Ser Leu Trp Pro Leu
760                 765                 770

TCA GTC GAA AGC CCA ATC GGA AGG TGC GGA GAA CCG AAT CGA TGT GTG  2465
Ser Val Glu Ser Pro Ile Gly Arg Cys Gly Glu Pro Asn Arg Cys Val
    775                 780                 785

CCA CAT ATT GAA TGG AAT CCT GAT TTA GAT TGT TCG TGT AGG GAT GGG  2513
Pro His Ile Glu Trp Asn Pro Asp Leu Asp Cys Ser Cys Arg Asp Gly
790                 795                 800                 805

GAG AAG TGT GCC CAT CAT TCG CAT CAT TTC TCT CTA GAT ATT GAT GTT  2561
Glu Lys Cys Ala His His Ser His His Phe Ser Leu Asp Ile Asp Val
        810                 815                 820

GGA TGT ACA GAC AAT GAG CTA GAC CTA GGT GTA TGG GTG ATC TTT AAG  2609
Gly Cys Thr Asp Asn Glu Leu Asp Leu Gly Val Trp Val Ile Phe Lys
825                 830                 835

ATT AAA ACG CAG GAT GGC CAT GCA AGA TTA GGA AAT CTA GAG TTT CTC  2657
Ile Lys Thr Gln Asp Gly His Ala Arg Leu Gly Asn Leu Glu Phe Leu
    840                 845                 850

GAA GAG AAA CCA TTG TTA GGA GAA GCG TTA GCT CGT GTG AAA AGA GCG  2705
Glu Glu Lys Pro Leu Leu Gly Glu Ala Leu Ala Arg Val Lys Arg Ala
855                 860                 865

GAG AAA AAA TGG AGA GAC AAA CGC GAA CAA TTG CAG TTT GAA ACG AAT  2753
Glu Lys Lys Trp Arg Asp Lys Arg Glu Gln Leu Gln Phe Glu Thr Asn
870                 875                 880                 885
```

FIGURE 1H

```
ATC GTT TAC AAA GAG GCA AAA GAA TCT GTA GAT GCT TTA TTC GTA GAT    2801
Ile Val Tyr Lys Glu Ala Lys Glu Ser Val Asp Ala Leu Phe Val Asp
        890                 895                 900

TCT CAC TAT AAT AGA TTA CAA GCG GAT ACG AAC ATT ACG ATG ATT CAT    2849
Ser His Tyr Asn Arg Leu Gln Ala Asp Thr Asn Ile Thr Met Ile His
            905                 910                 915

GCG GCA GAT AAA CGC GTT CAT CGA ATC CGA GAG GCT TAT CTT CCG GAA    2897
Ala Ala Asp Lys Arg Val His Arg Ile Arg Glu Ala Tyr Leu Pro Glu
        920                 925                 930

TTA TCC GTT ATC CCA GGT GTA AAT GCG GAC ATT TTT GAA GAA TTA GAA    2945
Leu Ser Val Ile Pro Gly Val Asn Ala Asp Ile Phe Glu Glu Leu Glu
        935                 940                 945

GGT CTT ATT TTC ACT GCA TTC TCC CTA TAT GAT GCG AGA AAT ATC ATT    2993
Gly Leu Ile Phe Thr Ala Phe Ser Leu Tyr Asp Ala Arg Asn Ile Ile
        950                 955                 960                 965

AAA AAC GGT GAT TTC AAT AAT GGT TTA TCG TGT TGG AAC GTG AAA GGG    3041
Lys Asn Gly Asp Phe Asn Asn Gly Leu Ser Cys Trp Asn Val Lys Gly
        970                 975                 980

CAT GTA GAT ATA CAA CAG AAT CAT CGT TCT GTC CTC GTT GTC CCG        3089
His Val Asp Ile Gln Gln Asn His Arg Ser Val Leu Val Pro
        985                 990                 995

GAA TGG GAA TCA GAG GTA TCA CAA GAA GTC CGC GTA TGT CCA GGT CGT    3137
Glu Trp Glu Ser Glu Val Ser Gln Glu Val Arg Val Cys Pro Gly Arg
        1000                1005                1010
```

FIGURE 1I

```
GGC TAT ATT CTT CGT GTC ACA GCG TAC AAA GAG GGC TAC GGA GAA GGA    3185
Gly Tyr Ile Leu Arg Val Thr Ala Tyr Lys Glu Gly Tyr Gly Glu Gly
1015                     1020                    1025

TGC GTA ACG ATC CAT GAG ATC GAA GAC AAT ACA GAC GAA TTG AAG TTT    3233
Cys Val Thr Ile His Glu Ile Glu Asp Asn Thr Asp Glu Leu Lys Phe
1030                    1035                    1040                    1045

AGT AAC TGC ATA GAA GAG GAA GTC TAT CCA ACG GAT ACA GGT AAT GAT    3281
Ser Asn Cys Ile Glu Glu Glu Val Tyr Pro Thr Asp Thr Gly Asn Asp
              1050                    1055                    1060

TAT ACT GCA CAC CAA GGT ACA ACA GGA TGC GCA GAT GCA TGT AAT TCC    3329
Tyr Thr Ala His Gln Gly Thr Thr Gly Cys Ala Asp Ala Cys Asn Ser
         1065                    1070                    1075

CGT AAT GTT GGA TAT GAG GAT GGA TAT GAA ATA AAT ACT ACA GCA TCT    3377
Arg Asn Val Gly Tyr Glu Asp Gly Tyr Glu Ile Asn Thr Thr Ala Ser
         1080                    1085                    1090

GTT AAT TAC AAA CCG ACT TAT GAA GAA GAA ATG TAT ACA GAT GTA CGA    3425
Val Asn Tyr Lys Pro Thr Tyr Glu Glu Glu Met Tyr Thr Asp Val Arg
1095                    1100                    1105

AGA GAT AAT CAT TGT GAA TAT GAC AGA GGA TAT GGG AAC CAT ACA CCG    3473
Arg Asp Asn His Cys Glu Tyr Asp Arg Gly Tyr Gly Asn His Thr Pro
1110                    1115                    1120                    1125

TTA CCA GCT GGT TAT GTA ACA AAA GAA TTA GAG TAC TTC CCT GAA ACA    3521
Leu Pro Ala Gly Tyr Val Thr Lys Glu Leu Glu Tyr Phe Pro Glu Thr
              1130                    1135                    1140
```

FIGURE 1J

```
GAT ACA GTA TGG ATA GAG ATT GGA GAA ACG GAA GGA ACA TTC ATC GTA
Asp Thr Val Trp Ile Glu Ile Gly Glu Thr Glu Gly Thr Phe Ile Val
            1145                    1150                    1155      3569

GAT AGT GTG GAA TTA CTC CTC ATG GAG GAA TAAGATTGTA CGAAATCGAC         3619
Asp Ser Val Glu Leu Leu Leu Met Glu Glu
            1160                    1165

TTTAAATGGC TCATTCTAAA CAAAAAGTAG TCGTCTAATC TCTGTAACAA ATAGAAAAGT    3679

AAATATTTGT AGAAAAAAGA AAAGGACAT TACT                                  3713
```

FIGURE 2A

```
AAACTATTCA ATGGAGAAAA ATTGAATAGT TGTAATGTAA GCACACCGAA AAAAGGAGGA         60

GTTATA TTG ACT TCA AAT AGG AAA AAT GAG AAT GAA ATT ATA AAT GCT          108
       Leu Thr Ser Asn Arg Lys Asn Glu Asn Glu Ile Ile Asn Ala
                        1                   5                  10

TTA TCG ATT CCA ACG GTA TCG AAT CCT TCC ACG CAA ATG AAT CTA TCA         156
Leu Ser Ile Pro Thr Val Ser Asn Pro Ser Thr Gln Met Asn Leu Ser
 15                  20                  25                  30

CCA GAT GCT CGT ATT GAA GAT AGC TTG TGT GTA GCC GAG GTG AAC AAT         204
Pro Asp Ala Arg Ile Glu Asp Ser Leu Cys Val Ala Glu Val Asn Asn
                 35                  40                  45

ATT GAT CCA TTT GTT AGC GCA TCA ACA GTC CAA ACG GGT ATA AAC ATA         252
Ile Asp Pro Phe Val Ser Ala Ser Thr Val Gln Thr Gly Ile Asn Ile
             50                  55                  60

GCT GGT AGA ATA TTG GGC GTA TTA GGT GTG CCG TTT GCT GGA CAA CTA         300
Ala Gly Arg Ile Leu Gly Val Leu Gly Val Pro Phe Ala Gly Gln Leu
         65                  70                  75

GCT AGT TTT TAT AGT TTT CTT GTT GGG GAA TTA TGG CCT AGT GGC AGA         348
Ala Ser Phe Tyr Ser Phe Leu Val Gly Glu Leu Trp Pro Ser Gly Arg
     80                  85                  90

GAT CCA TGG GAA ATT TTC CTG GAA CAT GTA GAA CAA CTT ATA AGA CAA         396
Asp Pro Trp Glu Ile Phe Leu Glu His Val Glu Gln Leu Ile Arg Gln
 95                 100                 105                 110

CAA GTA ACA GAA AAT ACT AGG AAT ACG GCT ATT GCT CGA TTA GAA GGT         444
Gln Val Thr Glu Asn Thr Arg Asn Thr Ala Ile Ala Arg Leu Glu Gly
                115                 120                 125
```

FIGURE 2B

```
CTA GGA AGA GGC TAT AGA TCT TAC CAG CAG GCT CTT GAA ACT TGG TTA    492
Leu Gly Arg Gly Tyr Arg Ser Tyr Gln Gln Ala Leu Glu Thr Trp Leu
         130                 135                 140

GAT AAC CGA AAT GAT GCA AGA TCA AGA AGC ATT ATT CTT GAG CGC TAT    540
Asp Asn Arg Asn Asp Ala Arg Ser Arg Ser Ile Ile Leu Glu Arg Tyr
         145                 150                 155

GTT GCT TTA GAA CTT GAC ATT ACT ACT GCT ATA CCG TTC AGA ATA        588
Val Ala Leu Glu Leu Asp Ile Thr Thr Ala Ile Pro Phe Arg Ile
         160                 165                 170

CGA AAT GAA GTT CCA TTA ATG GTA TAT GCT CAA GCT AAT                636
Arg Asn Glu Glu Val Pro Leu Met Val Tyr Ala Gln Ala Asn
         175                 180                 185                 190

TTA CAC CTA TTA TTG AGA GAC GCA TCC CTT TTT GGT AGT GAA TGG        684
Leu His Leu Leu Leu Arg Asp Ala Ser Leu Phe Gly Ser Glu Trp
         195                 200                 205

GGG ATG GCA TCT TCC GAT GTT AAC CAA TAT TAC CAA GAA CAA ATC AGA    732
Gly Met Ala Ser Ser Asp Val Asn Gln Tyr Tyr Gln Glu Gln Ile Arg
         210                 215                 220

TAT ACA GAG GAA TAT TCT AAC CAT TGC GTA CAA TGG TAT TAT AAT ACA GGG  780
Tyr Thr Glu Glu Tyr Ser Asn His Cys Val Gln Trp Tyr Tyr Asn Thr Gly
         225                 230                 235

CTA AAT AAC TTA AGA GGG ACA AAT GCT GAA AGT TGG CGG TAT AAT        828
Leu Asn Asn Leu Arg Gly Thr Asn Ala Glu Ser Trp Arg Tyr Asn
         240                 245                 250
```

FIGURE 2C

```
CAA TTC CGT AGA GAC CTA ACG TTA GGG GTA TTA GAT TTA GTA GCC CTA    876
Gln Phe Arg Arg Asp Leu Thr Leu Gly Val Leu Asp Leu Val Ala Leu
255                 260                 265                 270

TTC CCA AGC TAT GAT ACT CGC ACT TAT CCA ATC AAT ACG AGT GCT CAG    924
Phe Pro Ser Tyr Asp Thr Arg Thr Tyr Pro Ile Asn Thr Ser Ala Gln
                275                 280                 285

TTA ACA AGA GAA ATT TAT ACA GAT CCA ATT GGG AGA ACA AAT GCA CCT    972
Leu Thr Arg Glu Ile Tyr Thr Asp Pro Ile Gly Arg Thr Asn Ala Pro
        290                 295                 300

TCA GGA TTT GCA AGT ACG AAT TGG TTT AAT AAT GCA CCA TCG TTT        1020
Ser Gly Phe Ala Ser Thr Asn Trp Phe Asn Asn Ala Pro Ser Phe
305                 310                 315

TCT GCC ATA GAG GCT GCC ATT TTC AGG CCT CCG CAT CTA CTT GAT TTT    1068
Ser Ala Ile Glu Ala Ala Ile Phe Arg Pro Pro His Leu Leu Asp Phe
320                 325                 330

CCA GAA CAA CTT ACA ATT TAC AGT GCA TCA AGC CGT TGG AGT AGC ACT    1116
Pro Glu Gln Leu Thr Ile Tyr Ser Ala Ser Arg Trp Ser Ser Thr
335                 340                 345                 350

CAA CAT ATG AAT TAT TGG GTG GGA CAT AGG CTT AAC TTC CGC CCA ATA    1164
Gln His Met Asn Tyr Trp Val Gly His Arg Leu Asn Phe Arg Pro Ile
            355                 360                 365

GGA GGG ACA TTA AAT ACC TCA ACA CAA GGA CTT ACT AAT AAT ACT TCA    1212
Gly Gly Thr Leu Asn Thr Ser Thr Gln Gly Leu Thr Asn Asn Thr Ser
370                 375                 380
```

FIGURE 2D

```
ATT AAT CCT GTA ACA TTA CAG TTT ACG TCT CGA GAC GTT TAT AGA ACA    1260
Ile Asn Pro Val Thr Leu Gln Phe Thr Ser Arg Asp Val Tyr Arg Thr
385                         390                 395

GAA TCA AAT GCA GGG ACA AAT ATA CTA TTT ACT ACT CCT GTG AAT GGA    1308
Glu Ser Asn Ala Gly Thr Asn Ile Leu Phe Thr Thr Pro Val Asn Gly
400                         405                 410

GTA CCT TGG GCT AGA TTT AAT TTT ATA AAC CCT CAG AAT ATT TAT GAA    1356
Val Pro Trp Ala Arg Phe Asn Phe Ile Asn Pro Gln Asn Ile Tyr Glu
415                         420                 425             430

AGA GGC GCC ACT ACC TAC AGT CAA CCG TAT CAG GGA GTT GGG ATT CAA    1404
Arg Gly Ala Thr Thr Tyr Ser Gln Pro Tyr Gln Gly Val Gly Ile Gln
435                         440                 445

TTA TTT GAT TCA GAA ACT GAA TTA CCA GAA ACA ACA GAA CGA CCA        1452
Leu Phe Asp Ser Glu Thr Glu Leu Pro Glu Thr Thr Glu Arg Pro
450                         455                 460

AAT TAT GAA TCA TAT AGT CAT AGA TTA TCT CAT ATA GGA CTA ATC ATA    1500
Asn Tyr Glu Ser Tyr Ser His Arg Leu Ser His Ile Gly Leu Ile Ile
465                         470                 475

GGA AAC ACT TTG AGA GCA CCA GTC TAT TCT TGG ACG CAT CGT AGT GCA    1548
Gly Asn Thr Leu Arg Ala Pro Val Tyr Ser Trp Thr His Arg Ser Ala
480                         485                 490

GAT CGT ACG AAT ACG ATT GGA CCA AAT AGA ATT ACA CAA ATA CCA TTG    1596
Asp Arg Thr Asn Thr Ile Gly Pro Asn Arg Ile Thr Gln Ile Pro Leu
495                 500                 505             510
```

FIGURE 2E

```
GTA AAA GCA CTG AAT CTT CAT TCA GGT GTT ACT GTT GGA GGG CCA       1644
Val Lys Ala Leu Asn Leu His Ser Gly Val Thr Val Gly Gly Pro
            515                 520                 525

GGA TTT ACA GGT GGG GAT ATC CTT CGT AGA ACA AAT ACG GGT ACA TTT   1692
Gly Phe Thr Gly Gly Asp Ile Leu Arg Arg Thr Asn Thr Gly Thr Phe
                530                 535                 540

GGA GAT ATA CGA TTA AAT ATT AAT GTG CCA TTA TCC CAA AGA TAT CGC   1740
Gly Asp Ile Arg Leu Asn Ile Asn Val Pro Leu Ser Gln Arg Tyr Arg
            545                 550                 555

GTA AGG ATT CGT TAT GCT TCT ACT ACA GAT TTA CAA TTT CAA ACG AGA   1788
Val Arg Ile Arg Tyr Ala Ser Thr Thr Asp Leu Gln Phe Phe Thr Arg
    560                 565                 570

ATT AAT GGA ACC ACT GTT AAT ATT GGT AAT TTC TCA AGA ACT ATG AAT   1836
Ile Asn Gly Thr Thr Val Asn Ile Gly Asn Phe Ser Arg Thr Met Asn
        575                 580                 585         590

AGG GGG GAT AAT TTA GAA TAT AGA AGT TTT AGA ACT GCA GGA TTT AGT   1884
Arg Gly Asp Asn Leu Glu Tyr Arg Ser Phe Arg Thr Ala Gly Phe Ser
                595                 600                 605

ACT CCT TTT AAT TTT TTA AAT GCC CAA AGC ACA TTC ACA TTG GGT GCT   1932
Thr Pro Phe Asn Phe Leu Asn Ala Gln Ser Thr Phe Thr Leu Gly Ala
            610                 615                 620

CAG AGT TTT TCA AAT CAG GAA GTT TAT ATA GAT AGA GTC GAA TTT GTT   1980
Gln Ser Phe Ser Asn Gln Glu Val Tyr Ile Asp Arg Val Glu Phe Val
    625                 630                 635
```

FIGURE 2F

```
CCA GCA GAG GTA ACA TTT GAG GCA GAA TAT GAT TTA GAA AGA GCA CAA    2028
Pro Ala Glu Val Thr Phe Glu Ala Glu Tyr Asp Leu Glu Arg Ala Gln
640                 645                 650

AAG GCG GTG AAT GCT CTG TTT ACT TCT ACA AAT CCA AGA AGA TTG AAA    2076
Lys Ala Val Asn Ala Leu Phe Thr Ser Thr Asn Pro Arg Arg Leu Lys
        655                 660                 665            670

ACA GAT GTG ACA GAT TAT CAT ATT GAC CAA GTG TCC AAT ATG GTG GCA    2124
Thr Asp Val Thr Asp Tyr His Ile Asp Gln Val Ser Asn Met Val Ala
            675                 680                 685

TGT TTA TCA GAT GAA TTT TGC TTG GAT AAG CGA GAA TTA TTT GAG        2172
Cys Leu Ser Asp Glu Phe Cys Leu Asp Lys Arg Glu Leu Phe Glu
                690                 695                 700

AAA GTG AAA TAT GCG AAG CGA CTC AGT GAT GAA AGA AAC TTA CTC CAA    2220
Lys Val Lys Tyr Ala Lys Arg Leu Ser Asp Glu Arg Asn Leu Leu Gln
705                 710                 715

GAT CCA AAC TTC ACA TTC ATC AGT GGG CAA TTA AGT TTC GCA TCC ATC    2268
Asp Pro Asn Phe Thr Phe Ile Ser Gly Gln Leu Ser Phe Ala Ser Ile
720                 725                 730

GAT GGA CAA TCA AAC TTC CCC TCT ATT AAT GAG CTA TCT GAA CAT GGA    2316
Asp Gly Gln Ser Asn Phe Pro Ser Ile Asn Glu Leu Ser Glu His Gly
        735                 740                 745            750

TGG TGG GGA AGT GCG AAT GTT ACC ATT CAG GAA GGG AAT GAC GTA TTT    2364
Trp Trp Gly Ser Ala Asn Val Thr Ile Gln Glu Gly Asn Asp Val Phe
            755                 760                 765
```

FIGURE 2G

```
AAA GAG AAT TAC GTC ACA CTA CCG GGT ACT TTT AAT GAG TGT TAT CCA    2412
Lys Glu Asn Tyr Val Thr Leu Pro Gly Thr Phe Asn Glu Cys Tyr Pro
            770                 775                 780

AAT TAT TTA TAT CAA AAA ATA GGA GAG TCA GAA TTA AAA GCT TAT ACG    2460
Asn Tyr Leu Tyr Gln Lys Ile Gly Glu Ser Glu Leu Lys Ala Tyr Thr
        785                 790                 795

CGC TAT CAA TTA AGA GGG TAT ATT GAA GAT AGT CAA GAT CTA GAG ATT    2508
Arg Tyr Gln Leu Arg Gly Tyr Ile Glu Asp Ser Gln Asp Leu Glu Ile
    800                 805                 810

TAT TTA ATT CGT TAC AAT GCA AAG CAT GAA ACA TTG GAT GTT CCA GGT    2556
Tyr Leu Ile Arg Tyr Asn Ala Lys His Glu Thr Leu Asp Val Pro Gly
815                 820                 825                 830

ACC GAT TCC CTA TGG CCG CTT TCA GTT GAA AGC CCA ATC GGA AGG TGC    2604
Thr Asp Ser Leu Trp Pro Leu Ser Val Glu Ser Pro Ile Gly Arg Cys
            835                 840                 845

GGA GAA CCA AAT CGA TGC GCA CCA CAT TTT GAA TGG AAT CCT GAT CTA    2652
Gly Glu Pro Asn Arg Cys Ala Pro His Phe Glu Trp Asn Pro Asp Leu
        850                 855                 860

GAT TGT TCC TGC AGA GAT GGA GAA AGA TGT GCG CAT CAT CAT TCC CAT CAT    2700
Asp Cys Ser Cys Arg Asp Gly Glu Arg Cys Ala His His Ser His His
    865                 870                 875

TTC ACT TTG GAT ATT GAT GTT GGG TGC ACA GAC TTG CAT GAG AAC CTA    2748
Phe Thr Leu Asp Ile Asp Val Gly Cys Thr Asp Leu His Glu Asn Leu
880                 885                 890
```

FIGURE 2H

```
GGC GTG TGG GTG GTA TTC AAG ATT AAG ACG CAG GAA GGT TAT GCA AGA      2796
Gly Val Trp Val Val Phe Lys Ile Lys Thr Gln Glu Gly Tyr Ala Arg
895                 900                 905                 910

TTA GGA AAT CTG GAA TTT ATC GAA GAG AAA CCA TTA ATT GGA GAA GCA      2844
Leu Gly Asn Leu Glu Phe Ile Glu Glu Lys Pro Leu Ile Gly Glu Ala
            915                 920                 925

CTG TCT CGT GTG AAG AGA GCG GAA AAA TGG AGA GAC AAA CGG GAA          2892
Leu Ser Arg Val Lys Arg Ala Glu Lys Trp Arg Asp Lys Arg Glu
    930                 935                 940

AAA CTA CAA TTG GAA ACA AAA CGA GTA TAT ACA GAG GCA AAA GAA GCT      2940
Lys Leu Gln Leu Glu Thr Lys Arg Val Tyr Thr Glu Ala Lys Glu Ala
945                 950                 955

GTG GAT GCT TTA TTC GTA GAT TCT CAA TAT GAT CAA TTA CAA GCG GAT      2988
Val Asp Ala Leu Phe Val Asp Ser Gln Tyr Asp Gln Leu Gln Ala Asp
            965                 970

ACA AAC ATT GGC ATG ATT CAT GCG GCA GAT AAA CTT GTT CAT CGA ATT      3036
Thr Asn Ile Gly Met Ile His Ala Ala Asp Lys Leu Val His Arg Ile
975                 980                 985                 990

CGA GAG GCG TAT CTT TCA GAA TTA CCT GTT ATC CCA GGT GTA AAT GCG      3084
Arg Glu Ala Tyr Leu Ser Glu Leu Pro Val Ile Pro Gly Val Asn Ala
            995                 1000                1005

GAA ATT TTT GAA GAA TTA GAA GGT CAC ATT ATC ACT GCA ATG TCC TTA      3132
Glu Ile Phe Glu Glu Leu Glu Gly His Ile Ile Thr Ala Met Ser Leu
1010                1015                1020
```

FIGURE 21

```
TAC GAT GCG AGA AAT GTC GTT AAA AAT GGT GAT TTT AAT AAT GGA TTA    3180
Tyr Asp Ala Arg Asn Val Val Lys Asn Gly Asp Phe Asn Asn Gly Leu
              1025                    1030                1035

ACA TGT TGG AAT GTA AAA GGG CAT GTA GAT GTA CAA CAG AGC CAT CAT    3228
Thr Cys Trp Asn Val Lys Gly His Val Asp Val Gln Gln Ser His His
          1040                    1045                    1050

CGT TCT GAC CTT GTT ATC GAA CCA GAA TGG GAA GCA GAA GTG TCA CAA GCA    3276
Arg Ser Asp Leu Val Ile Glu Pro Glu Trp Glu Ala Glu Val Ser Gln Ala
      1055                    1060                    1065         1070

GTT CGC GTC TGT CCG GGG CGT GGC TAT ATC CTT CGT GTC ACA GCG TAC    3324
Val Arg Val Cys Pro Gly Arg Gly Tyr Ile Leu Arg Val Thr Ala Tyr
                  1075                    1080                1085

AAA GAG GGA TAT GGA GAG GGC TGC GTA ACG ATC CAT GAA ATC GAG AAC    3372
Lys Glu Gly Tyr Gly Glu Gly Cys Val Thr Ile His Glu Ile Glu Asn
      1090                    1095                    1100

AAT ACA GAC GAA CTA AAA TTT AAA AAC TGT GAA GAA GAG GTG TAT    3420
Asn Thr Asp Glu Leu Lys Phe Lys Asn Cys Glu Glu Glu Val Tyr
              1105                    1110                1115

CCA ACG GAT ACA GGA ACG TGT AAT GAT TAT ACT GCA CAC CAA GGT ACA    3468
Pro Thr Asp Thr Gly Thr Cys Asn Asp Tyr Thr Ala His Gln Gly Thr
          1120                    1125                    1130

GCA GCA TGT AAT TCC CGT AAT GCT GGA TAT GAG GAT GCA TAT GAA GTT    3516
Ala Ala Cys Asn Ser Arg Asn Ala Gly Tyr Glu Asp Ala Tyr Glu Val
      1135                    1140                    1145     1150
```

FIGURE 2J

```
GAT ACT ACA GCA TCT GTT AAT TAC AAA CCG ACT TAT GAA GAA ACG       3564
Asp Thr Thr Ala Ser Val Asn Tyr Lys Pro Thr Tyr Glu Glu Thr
                1155                         1160            1165

TAT ACA GAT GTA CGA AGA GAT AAT CAT TGT GAA TAT GAC AGA GGG TAT   3612
Tyr Thr Asp Val Arg Arg Asp Asn His Cys Glu Tyr Asp Arg Gly Tyr
                1170                    1175              1180

GTG AAT TAT CCA CCA GTA CCA GCT GGT TAT GTG ACA AAA GAA TTA GAA   3660
Val Asn Tyr Pro Pro Val Pro Ala Gly Tyr Val Thr Lys Glu Leu Glu
                1185                     1190             1195

TAC TTC CCA GAA ACA GAT ACA GTA TGG ATT GAG ATT GGA GAA ACG GAA   3708
Tyr Phe Pro Glu Thr Asp Thr Val Trp Ile Glu Ile Gly Glu Thr Glu
        1200                      1205                  1210

GGA AAG TTT ATT GTA GAT AGC GTG GAT AGC GTG CTA CTC CTC ATG GAA GAA TAGGATCATG   3763
Gly Lys Phe Ile Val Asp Ser Val Glu Leu Leu Leu Met Glu Glu
        1215                   1220                   1225              123

CAAGTATAGC AGTTAATAA ATATTAATTA AAATAGTAGT CTAACTTCCG TTCCAATTAA   3823

ATAAGTAAAT TACAGTTGTA AAAAGAAAAC GGACATCACT CTTCAGAGAG CGATGTCCGT   3883

TTTTTATATG GTGTGTGCTA ATGATAAATG TGCACGAAAT TATATTGTCA A           3934
```

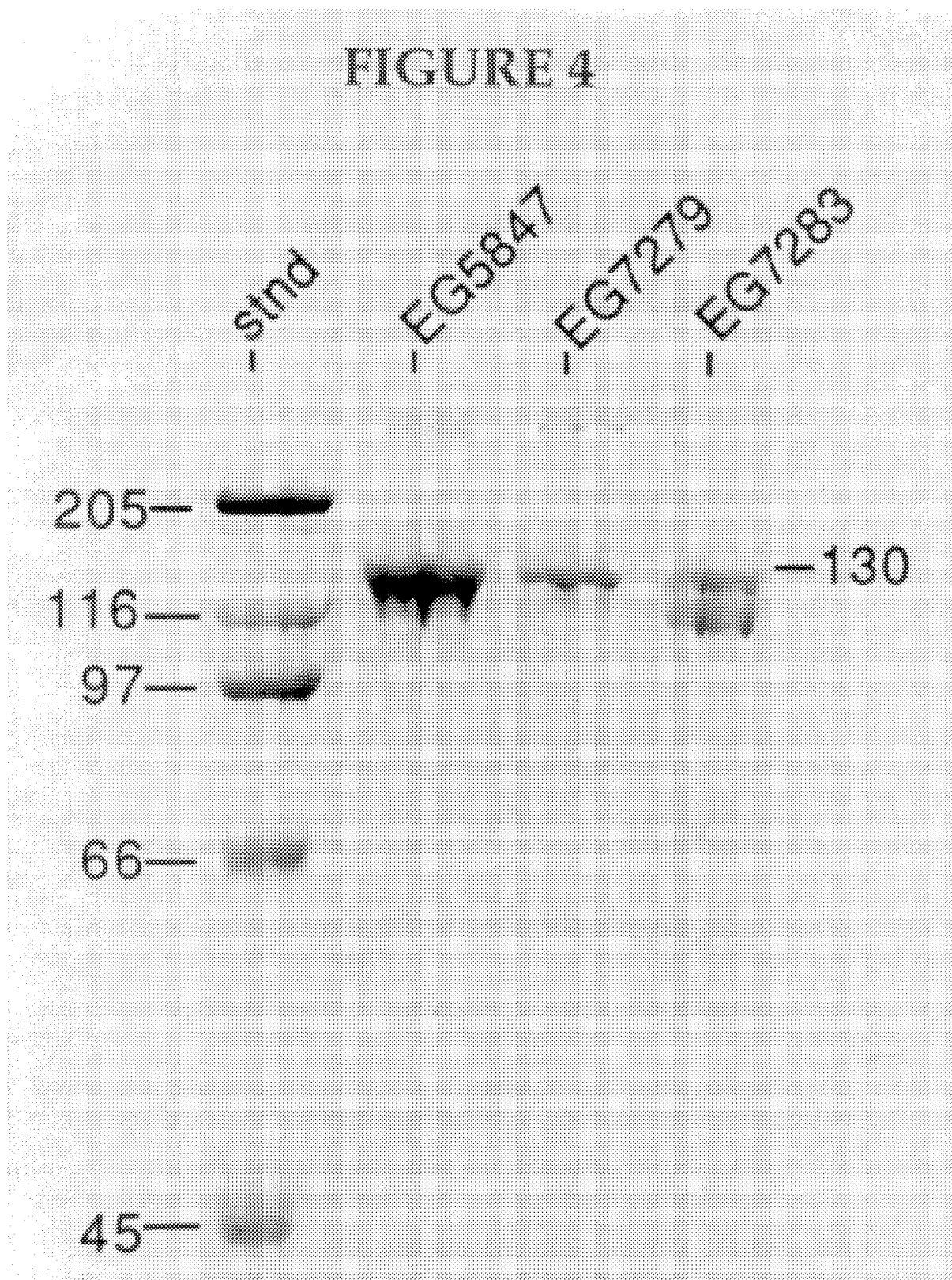

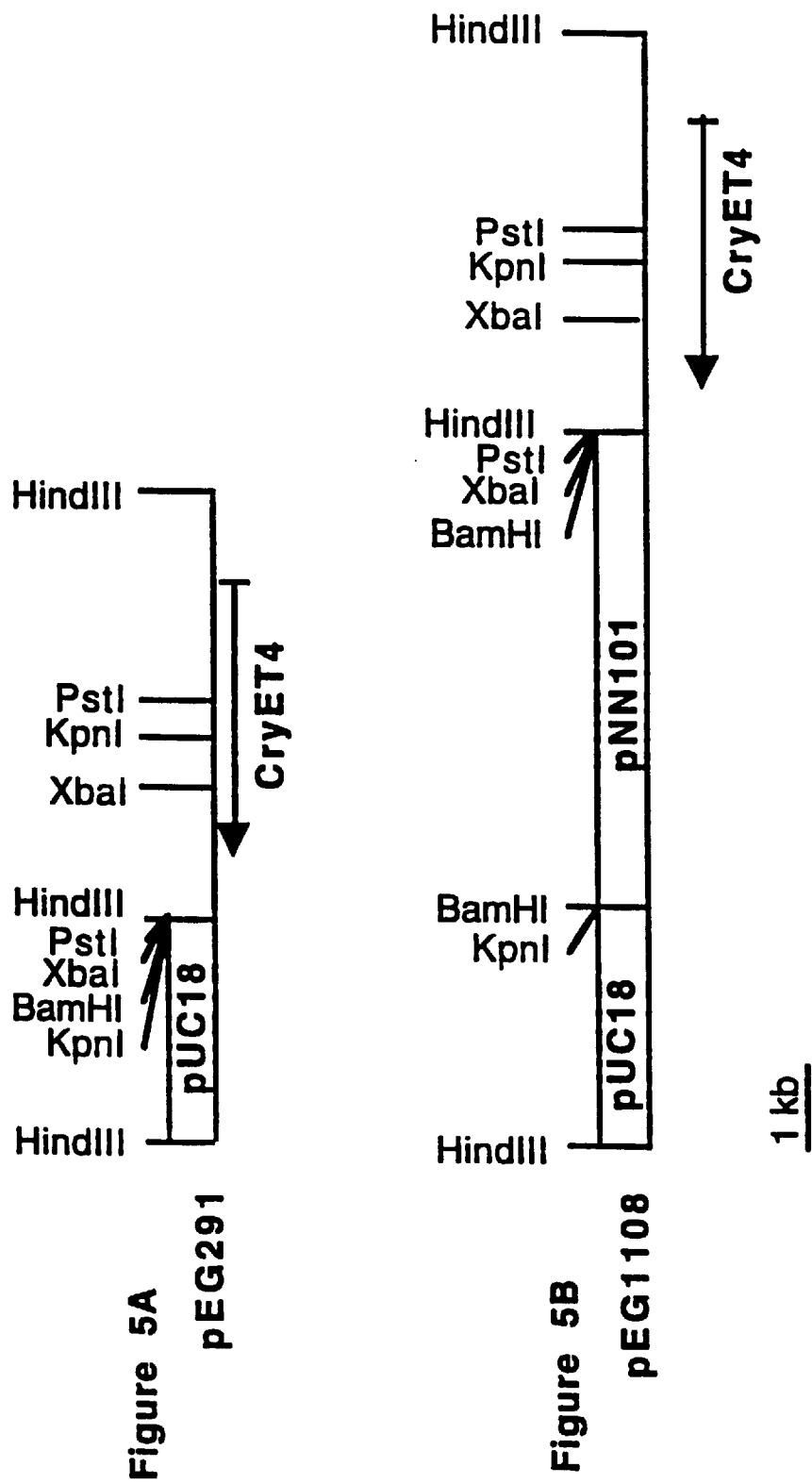
Figure 5A pEG291
Figure 5B pEG1108
1 kb

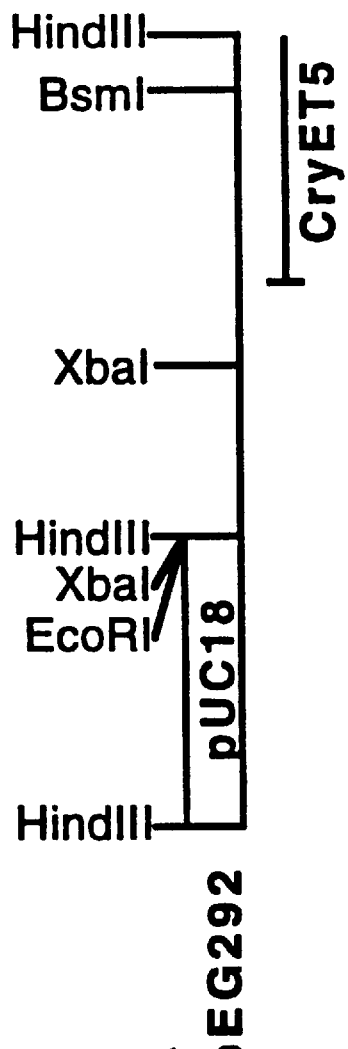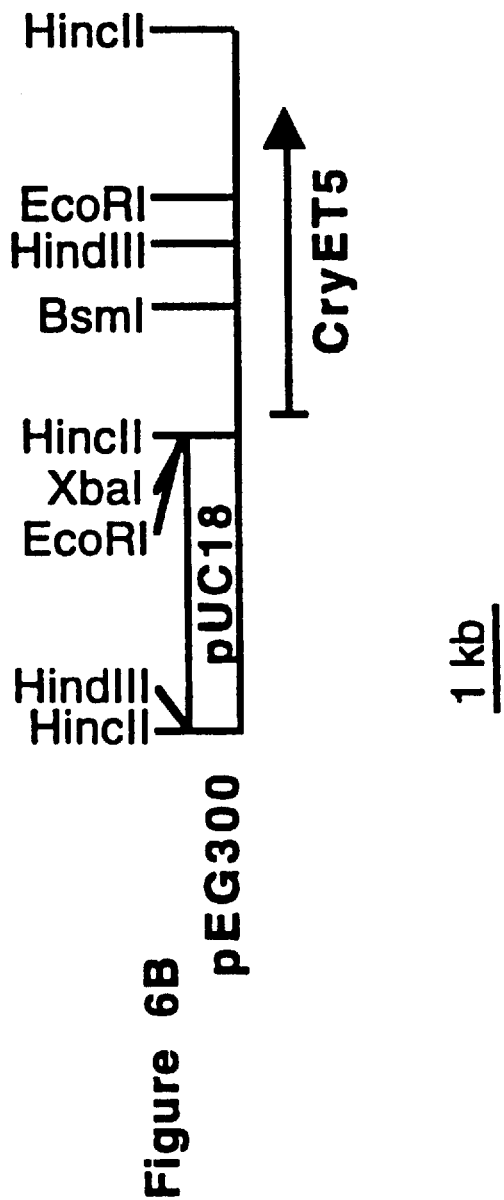
Figure 6A pEG292
Figure 6B pEG300

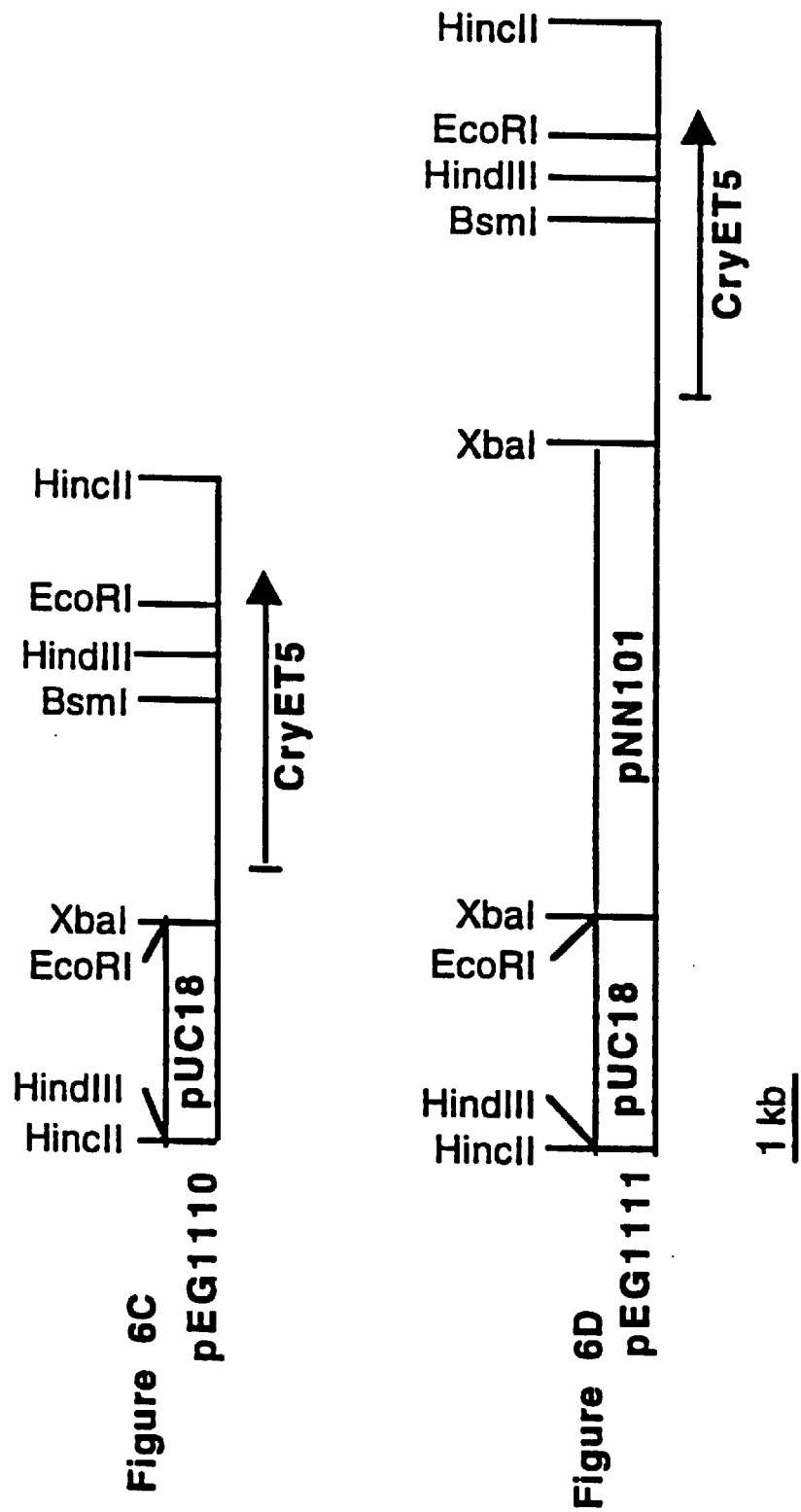

BACILLUS THURINGIENSIS BACTERIA

CROSS REFERENCE TO RELATED APPLICATION

This application is a division of U.S. patent application Ser. No. 08/474,038, filed Jun. 7, 1995, now U.S. Pat. No. 5,679,343, which is a division of U.S. patent application Ser. No. 08/176,865, filed Dec. 30, 1993, now U.S. Pat. No. 5,616,319, which is a division of U.S. patent application Ser. No. 08/100,709, filed Jul. 29, 1993, now U.S. Pat. No. 5,322,687.

FIELD OF THE INVENTION

The present invention relates to lepidopteran-toxic proteins and the genes coding therefor. In particular, the present invention is directed to genes designated as CryET4 (SEQ ID NO:1) and CryET5 (SEQ ID NO:3) and their proteins designated respectively as CryET4 (SEQ ID NO:2) and CryET5 (SEQ ID NO:4).

BACKGROUND OF THE INVENTION

Bacillus thuringiensis (commonly known as B.t.) is a gram-positive soil bacterium that often produces cellular inclusions during sporulation which are specifically toxic to certain orders and species of insects. Many different strains of B.t. have been shown to produce these inclusions of insecticidal crystal protein (ICP). Compositions including B.t. strains which produce insecticidal proteins have been commercially available and used as environmentally acceptable insecticides because they are quite toxic to the specific target insect, but are harmless to plants and other non-targeted organisms.

B.t. ICP toxins are active in the insect only after ingestion. After ingestion by an insect, the alkaline pH and proteolytic enzymes in the mid-gut solubilize the crystal allowing the release of the toxic components. These toxic components disrupt the mid-gut cells resulting in cessation of feeding and, eventually, death of the insect. B.t. has proven to be an effective and environmentally safe insecticide in dealing with various insect pests.

A number of genes encoding crystal proteins have been cloned from many strains of B.t. A good overview is set forth in H. Höfte and H. R. Whiteley, Microbiol. Rev., 53, pp. 242–255 (1989), hereinafter "Höfte and Whiteley (1989)." This reference provides a good overview of the genes and proteins obtained from B.t. and their uses, adopts a nomenclature and classification scheme for B.t. genes and proteins, and has an extensive bibliography.

The nucleotide sequences of ICP genes responsible for a given crystal phenotype and active against the same insect order are generally more related, i.e., more homologous, than are the nucleotide sequences of B.t. genes encoding delta-endotoxin proteins active against different orders of insects. Höfte and Whiteley (1989) defines an ordered classification of genes encoding B.t. delta-endotoxin proteins based on homology of delta-endotoxin amino acid sequences, as well as similarities in insecticidal activity; a subranking has also been established based upon further refinement of sequence relationship. As noted by Höfte and Whiteley (1989), the majority of insecticidal B.t. strains are active against insects of the order Lepidoptera, i.e., caterpillar insects. Insecticidal crystal proteins specifically active against Lepidoptera have been designated CryI proteins. These ICPs are encoded by cryI genes. Other B.t. strains produce different classes of crystal proteins, e.g., CryII proteins are active against lepidopteran and (for CryIIA) dipteran insects; CryIII proteins are insecticidal to insects of the order Coleoptera, i.e., beetles; and CryIV proteins are active against insects of the order Diptera, i.e., flies and mosquitoes. A compilation of the amino acid identities for several CryI proteins as well as CryII, CryIII and CryIV proteins has been determined in Hodgman and Ellar, J. DNA Sequencing and Mapping, 1, pp. 97–106 (1990).

The CryI family of ICPs contains the largest number of known toxin genes derived from B.t., as evidenced by the survey in Höfte and Whiteley (1989) and by subsequent reports of CryI-type ICPs.

Schnepf et al., J. Biol. Chem., 260, pp. 6264–6272 (1985), reported the complete nucleotide sequence for a toxin gene from B.t. kurstaki HD-1. This gene was subsequently classified as cryIA(a) by Höfte and Whiteley (1989). The published open reading frame extends 1176 amino acids and encodes a protein with a calculated molecular mass of 133,500 Daltons (Da). Another gene, also classified as cryIA(a), was isolated from B.t. subsp. kurstaki HD-1 Dipel® by Shibano et al., Gene 34, pp. 243–251 (1985). As detailed in Table 2 of Höfte and Whiteley (1989), this gene is highly related, especially in the N terminal moiety, to cryIA(a) reported by Schnepf et al. (1985). CryIA(a) protein is broadly active against Lepidoptera; Höfte and Whiteley (1989) reports that four of five tested lepidopteran insects were sensitive to this toxin.

Other ICP genes subsequently identified as cryIA(a) that are greater than 99% identical to the holotype cryIA(a) gene have been identified in B. thuringiensis subspecies aizawai, (Shimizu et al., Agric. Biol. Chem., 52, pp. 1565–1573 (1988)), subspecies kurstaki, (Kondo et al., Agric. Biol. Chem., 51, pp. 455–463 (1987)), and subspecies entomocidus (Masson et al., Nucleic Acids Res. 17, p. 446 (1989)). The cryI-type nucleotide sequence disclosed in European Patent Application Publication No. 0 367 474, published May 9, 1990, of Mycogen Corporation, reveals a DNA sequence related to the cryIA(a) gene and its encoded protein that is 92% positionally identical to the holotype CryIA(a) ICP.

Wabiko et al., DNA, 5, pp. 305–314 (1986), describe the DNA sequence of an insecticidal toxin gene from B.t. subsp. berliner 1715, subsequently classified as cryIA(b) by Höfte and Whiteley (1989). The molecular mass of the protein encoded is 130,615 Da and sequential deletions indicate that the $NH_2$-terminal 612 amino acid polypeptide is toxic to lepidopteran insects. Höfte et al., Eur. J. Biochem., 161, pp. 273–280 (1986), describe the cloning and nucleotide sequencing of a variant crystal protein gene from B.t. subsp. berliner 1715, subsequently also classified as cryIA(b). The cloned gene produces an approximately 130,000 Da protein which coincides with the mass of the major protein observed in the strain. The gene has an open reading frame of 3465 bases which would encode a protein 1155 amino acids in length having a mass of 130,533 Da. Similarities of this sequence to the previously reported sequences for the cloned crystal genes from B.t. kurstaki HD-1, B.t. kurstaki HD-73 and B.t. sotto are discussed in the Höfte et al. (1986) paper. Data identifying a minimal toxic fragment required for insecticidal activity are also presented. The cryIA(b) gene discussed in Höfte et al. (1986) differs in its deduced amino acid sequence by only two amino acids from the CryIA(b) protein reported by Wabiko et al.

Other cryIA(b) genes have been disclosed in Geiser et al., Gene, 48, pp. 109–118 (1986), Hefford et al., J. Biotechnol., 6, pp. 307–322 (1987), Oeda et al., Gene, 53, pp. 113–119

(1987), Kondo et al., supra, Fischhoff et al., *Bio/Technology*, 5, pp. 807–813 (1987) and Haider and Ellar, *Nucl. Acids Res.*, 16, p. 10927 (1988). Each of these six CryIA(b) ICPs is greater than 99% positionally identical to the holotype CryIA(b) toxin.

Adang et al., *Gene*, 36, pp. 289–300 (1985), report the cloning and complete nucleotide sequence of a crystal protein gene harbored on the 75 kilobase (kb) plasmid of strain *B.t.* subsp. kurstaki Hd-73. The restriction map in the article identified this gene as holotype cryIA(c) under the current classification system of Höfte and Whiteley (1989). The complete sequence of the gene, spanning 3537 nucleotide base pairs (bp), coding for 1178 amino acids and potentially encoding a protein of 133,330 Da, is shown in the article. Toxicity data against *Manduca sexta* for the protein made by the cryIA(c) gene are also presented. CryIA(c) toxins have been isolated from several strains of *B.t.* subsp. *kenyae* that are highly related to the above-noted CryIA(c) toxin from *B.t.* subsp. *kurstaki* (greater than 99% positionally identical in deduced amino acid sequence) but whose protein products, although broadly active against lepidopteran insects, nonetheless show quantitatively different toxicities for individual insect species (Von Tersch et al., *Appl. Environ. Microbiol.*, 57, pp. 349–358 (1991)).

Brizzard et al., *Nucleic Acids Res.*, 16, pp. 2723–2724 (1988), describe the nucleotide sequence of crystal protein gene cryA4 (subsequently classified as cryIB by Höfte and Whiteley (1989)) isolated from *B.t.* subsp. *thuringiensis* HD-2. Höfte and Whiteley (1989) report an insecticidal specificity of CryIB toxin for *Pieris brassicae*.

Honee et al., *Nucleic Acids Res.*, 16, p. 6240 (1988), describe the complete DNA sequence for the BTVI crystal protein gene isolated from *B.t.* subsp. *entomocidus* 60.5 (holotype cryIC by Höfte and Whiteley (1989)). This protein is reported to exhibit enhanced insecticidal activities against Spodoptera species.

Sanchis et al., *Mol. Microbiol.*, 3, pp. 229–238 (1989) report the nucleotide sequence for the N-terminal coding region (2470 nucleotides) and 5' flanking region of a gene from *B.t.* subsp. *aizawai* 7.29 now classified as the cryIC gene under the classification system of Höfte and Whiteley (1989). Sanchis et al. disclose similar information about the cryIC gene in European Patent Application Publication No. 0 295 156, published Dec. 14, 1988. The open reading frame encodes a truncated polypeptide 824 amino acids long with a calculated mass of 92,906 Da.

A gene isolated from *B.t.* subspecies *aizawai* and now classified as holotype cryID under the Höfte and Whiteley (1989) system is disclosed in European Patent Application Publication No. 0 358 557, published Mar. 14, 1990 of Plant Genetic Systems, N.V. Höfte and Whiteley (1989) report selective lepidopteran toxicity against *Manduca Sexta* for the CryID protein, the CryID toxin being largely inactive against other lepidopteran insects tested.

The holotype cryIE gene, found in a *B.t.* subspecies *darmstadiensis* strain, is disclosed in European Patent Application Publication No. 0 358 557, supra. A highly related cryIE gene from *B.t.* subsp. *kenyae* is disclosed by Visser et al., *J. Bacteriol.*, 172, pp. 6783–6788 (1990).

Visser, *Mol. Gen. Genet.*, 212, pp. 219–224 (1988) report the isolation and analysis of five toxin genes belonging to four different gene families from *B.t. entomocidus* 60.5, one of which is reported by Honee et al. (1988), supra. Two of these genes, BTIV and BTVIII, are cryIA(a)-type genes according to the Höfte and Whiteley (1989) classification scheme. The BTVI gene, also reported by Honee et al. (1988) supra, is a cryIC gene according to the Höfte and Whiteley (1989) classification scheme. The authors state that the restriction map for another gene, designated BTV, closely resembles that identified for the cryID gene isolated from *B.t.* strain HD-68 subsp. *aizawai*, and disclosed in European Patent Application Publication No. 0 358 557, supra. A fifth gene, designated BTVII, is also identified and its restriction map differs significantly from the other four genes described. Toxicity data against several lepidopteran insects, *S. exigua, S. littoralis, H. virescens* and *P. brassicae*, are presented for each of the isolates. The BTV gene product was inactive against all insects tested. The BTVI protein is highly active against *Spodoptera larvae*, and the BTVII protein is toxic to *P. brassicae*.

Additional genes within the cryI family have been reported in the literature. A gene found in *B.t.* subsp. *aizawai* and described as cryIF is disclosed by Chambers et al. in *J. Bacteriol.*, 173, pp. 3966–3976 (1991) and in PCT International Publication No. WO91/16434, published Oct. 31, 1991. A gene described as cryIG from *B.t.* subsp. *galleria* is disclosed by Smulevitch et al., *FEBS Lett.*, 293, pp. 25–28 (1991). A gene that is highly related to the cryIG gene has been isolated from *B.t.* DSIR 517 by Gleave et al., *J. Gen. Microbiol.*, 138, pp. 55–62 (1992).

A novel gene related to cryI-type genes is disclosed in PCT International Publication No. WO 90/13651, published Nov. 15, 1990, of Imperial Chemical Industries PLC. This gene encodes an 81 kDa polypeptide (Cry pJH11) that is broadly insecticidal and more distantly related to the family of cryI sequences than are most other reported cryI- type sequences. Four cryI-type sequences are disclosed in European Patent Application Publication No. 0 405 810, published Jan. 2, 1991, of Mycogen Corporation. Inspection of the cryI-type sequences revealed that one of the disclosed genes (cry 81B2) belongs to the cryIC class, one (cry 81IB) belongs to the cryID class, and one (cry 81IA) belongs to the cryIF class. The fourth disclosed cryI sequence (cry 81IA2) appears to belong to a new class. Two cryI sequences are disclosed in European Patent Application Publication No. 0 401 979, published Dec. 12, 1990, of Mycogen Corporation. One of the disclosed sequences (PS82A2) appears to encode a novel gene, the other sequence (PS82RR) is highly related to the novel sequence cry 81IA2 disclosed in European Patent Application Publication No. 0 405 810.

Five novel cry sequences are disclosed in European Patent Application Publication No. 0 462 721, published Dec. 27, 1991, of Mycogen Corporation. These Cry proteins are reported to be nematocidal.

SUMMARY OF THE INVENTION

Briefly stated, one aspect of the present invention relates to a purified, isolated cryET4 gene having a nucleotide base sequence coding for the amino acid sequence shown in FIG. 1 and listed in SEQ ID NO:2.

The isolated cryET4 gene has a coding region extending from nucleotide bases 99 to 3602 (including the stop codon) in the nucleotide base sequence shown in FIG. 1 and listed in SEQ ID NO:1.

The present invention also relates to the isolated CryET4 protein which is obtainable from the cryET4 gene, and which has the amino acid sequence shown in FIG. 1 (SEQ ID NO:2), and which is insecticidal to lepidopteran insects.

Another aspect of the present invention relates to a purified, isolated cryET5 gene having a nucleotide base sequence coding for the amino acid sequence shown in FIG. 2 and listed in SEQ ID NO:4.

The isolated cryET5 gene has a coding region extending from nucleotide bases 67 to 3756 (including the stop codon) in the nucleotide base sequence shown in FIG. 2 and listed in SEQ ID NO:3.

The present invention also relates to the isolated CryET5 protein which is obtainable from the cryET5 gene, and which has the amino acid sequence shown in FIG. 2 (SEQ ID NO:4), and which is insecticidal to lepidopteran insects.

Additionally, the present invention relates to biologically pure cultures of a *Bacillus thuringiensis* bacterium designated as strain EG7279 transformed with a cryET4 gene having a coding region listed in SEQ ID NO:1 and strain EG7283 transformed with a cryET5 gene having a coding region listed in SEQ ID NO:3 or mutants thereof having insecticidal activity against lepidopteran insects susceptible to the CryET4 and CryET5 proteins, respectively.

The invention also relates to a biologically pure culture of a *Bacillus thuringiensis* bacterium designated as strain EG5847 or mutants thereof having insecticidal activity against lepidopteran insects susceptible to *B.t.* strain EG5847. *B.t.* strain EG5847 is a wild type isolate and is the *B.t.* strain from which the cryET4 and cryET5 genes were isolated.

Additional aspects of the present invention relate to recombinant plasmids containing the cryET4 and cryET5 genes; bacteria transformed with the recombinant plasmids and capable of expressing the cryET4 and/or cryET5 genes; insecticide compositions comprising the proteins and/or one or both of the transformed bacteria and/or other bacteria containing the CryET4 or CryET5 protein, with an agriculturally acceptable carrier; a method of controlling lepidopteran insects using the insecticides; plants transformed with and capable of expressing the cryET4 and/or cryET5 genes; and hybridization probes containing the cryET4 or cryET5 gene wherein the gene or at least an oligonucleotide portion of it is labeled for such use.

BRIEF DESCRIPTION OF THE DRAWINGS

FIG. 1 comprises FIGS. 1A through 1J and shows the nucleotide sequence of the cryET4 gene (SEQ ID NO:1) and the deduced amino acid sequence of the CryET4 protein (SEQ ID NO:2).

FIG. 2 comprises FIGS. 2A through 2J and shows the nucleotide sequence of the cryET5 gene (SEQ ID NO:3) and the deduced amino acid sequence of the CryET5 protein (SEQ ID NO:4).

FIG. 4 is a photograph of a Coomassie blue stained gel containing size-fractionated proteins from *B.t.* strains EG5847, EG7279 and EG7283, obtained by sodium dodecyl sulfate polyacrylamide gel electrophoresis (SDS-PAGE).

FIG. 5 comprises FIGS. 5A and 5B and is a restriction map of the recombinant plasmids pEG291 (6A) and pEG1108 (5B), both of which contain the cloned cryET4 gene. The location and orientation of the cryET4 gene are indicated by the arrow.

FIG. 6 comprises FIGS. 6A, 6B, 6C and 6D and is a restriction map of the recombinant plasmids pEG292 (6A), pEG300 (6B), pEG1110 (6C) and pEG1111 (6D). Plasmids pEG292 and pEG300 contain 5' and 3' portions of the cryET5 gene, respectively. Plasmids pEG1110 and pEG1111 contain the entire cloned cryET5 gene. The location and direction of transcription of the cryET5 gene are indicated by the arrows.

DETAILED DESCRIPTION OF THE PREFERRED EMBODIMENTS

Figure 3:
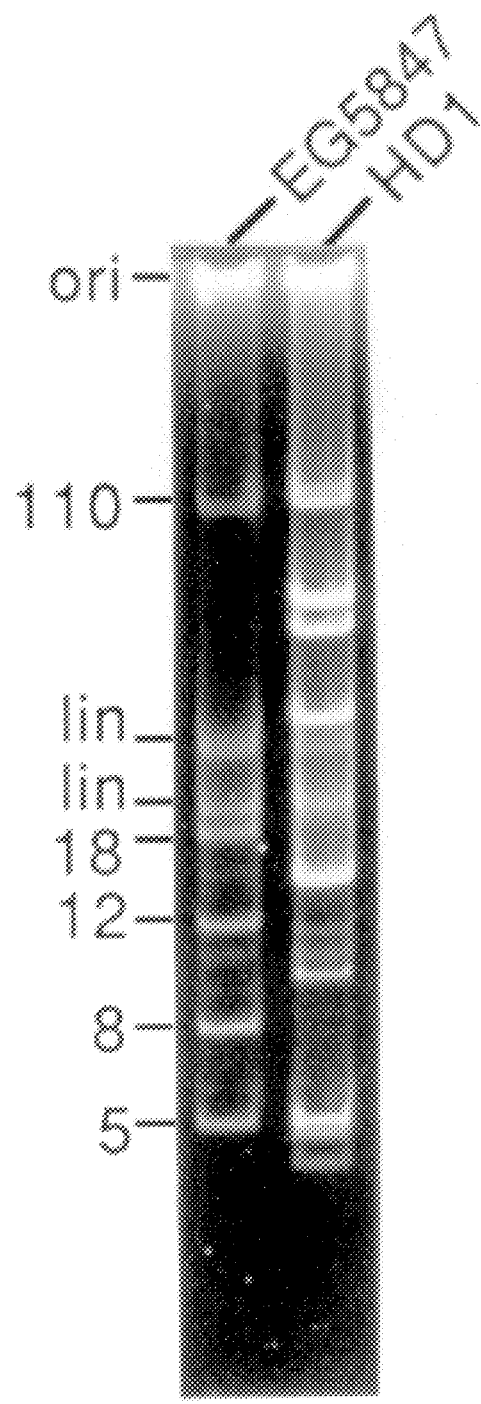
FIG. 3 is a photograph of an ethidium bromide stained agarose gel containing size-fractionated plasmids of *B.t.* strains EG5847 and HD-1, with plasmid sizes in megadaltons (MDa) being shown. The abbreviations in FIG. 3 are as follows: "ori" indicates the loading site and "lin" means linear DNA.

Two novel *Bacillus thuringiensis* (*B.t.*) toxin genes, designated cryET4 (SEQ ID NO:1) and cryET5 (SEQ ID NO:3), were obtained from a novel *B.t.* isolate designated EG5847. Isolation of *B.t.* strain EG5847, isolation of the novel toxin genes cryET4 and cryET5, construction of Bacillus/*E. coli* shuttle vectors containing cryET4 (pEG1108) and cryET5 (pEG1111), and transformation of pEG1108 and pEG1111 into a *B.t.* host (*B.t.* strain EG10368) to produce recombinant *B.t.* strains EG7279 and EG7283 expressing respectively the CryET4 (SEQ ID NO:2) and CryET5 (SEQ ID NO:4) toxin protein gene products, are described generally in the Examples.

Subcultures of *B.t.* strains EG5847, EG10368, EG7279 and EG7283 were deposited in the permanent collection of the Agricultural Research Service Culture Collection, Northern Regional Research Laboratory (NRRL), U.S. Department of Agriculture, 1815 North University Street, Peoria, Ill. 61604, U.S.A. The accession numbers and deposit dates are as follows:

| Subculture | Accession No. | Deposit Date |
| --- | --- | --- |
| B.t. EG5847 | NRRL B-21110 | June 9, 1993 |
| B.t. EG10368 | NRRL B-21125 | July 20, 1993 |
| B.t. EG7279 | NRRL B-21112 | June 9, 1993 |
| B.t. EG7283 | NRRL B-21111 | June 9, 1993 |

These microorganism deposits were made under the provisions of the "Budapest Treaty on the International Recognition of the Deposit of Microorganism for the Purposes of Patent Procedure." All restrictions on the availability to the public of these deposited microorganisms will be irrevocably removed upon issuance of a United States patent based on this application.

The present invention is intended to cover mutants and recombinant or genetically engineered derivatives, e.g., truncated versions, of the cryET4 gene listed in SEQ ID NO:1 and the cryET5 gene listed in SEQ ID NO:3 that yield a protein with insecticidal properties essentially the same as those of the CryET4 protein listed in SEQ ID NO:2 and the CryET5 protein listed in SEQ ID NO:4. Likewise, the present invention covers those gene nucleotide base sequences that encode the amino acid sequences of the CryET4 protein (SEQ ID NO:2) and the CryET5 protein (SEQ ID NO:4). Variations may be made in the cryET4 and cryET5 gene nucleotide base sequences shown in FIGS. 1 and 2, respectively, and listed in SEQ ID NO:1 and SEQ ID NO:3, respectively, which do not affect the amino acid sequence of the gene product, since the degeneracy of the genetic code is well known to those skilled in the art. Moreover, there may be some variations or truncations in the coding regions of the cryET4 and cryET5 nucleotide base sequences which allow expression of the gene and production of functionally equivalent forms of the CryET4 and CryET5 insecticidal proteins. These variations or truncations, which can be determined without undue experimentation by those of ordinary skill in the art with reference to the present specification, are to be considered within the scope of the appended claims, since they are fully equivalent to the specifically claimed subject matter.

It has been shown that proteins of identical structure and function may be constructed by changing the amino acid sequence, if such changes do not alter the protein secondary structure (Kaiser and Kezdy, Science, 223, pp. 249–255 (1984)). Single amino acid substitutions have been introduced by site-directed mutagenesis at various positions of CryIA(a) toxin protein without altering the insecticidal properties of the parent toxin (Ge et al., Proc. Natl. Acad. Sci. USA, 86, pp. 4037–4041 (1989)). The present invention includes mutants of the amino acid sequences disclosed herein which have an unaltered protein secondary structure or, if the structure is altered, where the mutant has retained substantially equivalent biological activity compared to the unaltered protein.

The cryET4 gene (SEQ ID NO:1) and cryET5 (SEQ ID NO:3) gene are also useful as DNA hybridization probes, for discovering similar or closely related cryET4-type and cryET5-type genes in other B.t. strains. The cryET4 gene (SEQ ID NO:1) and cryET5 gene (SEQ ID NO:3), or unique portions or derivatives thereof capable of hybridizing selectively to a target nucleic acid, e.g., homologous oligonucleotides of 12 or more nucleotides, or larger portions of the genes, that contain nucleotide sequences unique to the cryET4 gene or cryET5 gene and that are different from similar sized nucleotide segments in known, prior art B.t. toxin genes, can be labeled for use as hybridization probes using conventional procedures. An exemplary label is a radioactive label.

Both the cryET4 gene (SEQ ID NO:1), its corresponding insecticidal CryET4 protein (SEQ ID NO:2) and the cryET5 gene (SEQ ID NO:2) and its corresponding insecticidal CryET5 protein (SEQ ID NO:4) were first identified in B.t. strain EG5847, a novel B.t. isolate. The characteristics of B.t. strain EG5847 are more fully described in the Examples.

The gacillus strains described herein may be cultured using conventional growth media and standard fermentation techniques. The B.t. strains harboring the cryET4 gene (SEQ ID NO:1) or the cryET5 gene (SEQ ID NO:3), or both genes, may be fermented, as described in Example 1, until the cultured B.t. cells reach the stage of their growth cycle when the CryET4 crystal protein (SEQ ID NO:2) or the CryET5 crystal protein (SEQ ID NO:4) is formed. For sporogenous B.t. strains, fermentation is typically continued through the sporulation stage when the crystal protein is formed along with spores. The B.t. fermentation culture is then typically harvested by centrifugation, filtration or the like to separate fermentation culture solids containing the crystal protein from the culture medium.

The separated fermentation solids are primarily CryET4 crystal protein (SEQ ID NO:2) or CryET5 crystal protein (SEQ ID NO:4) and B.t. spores (if a sporulating host is employed), along with some cell debris, some intact cells and residual fermentation medium solids. If desired, the crystal protein may be separated from the other recovered solids via conventional methods, e.g., density gradient fractionation.

The B.t. strains exemplified in this disclosure are sporulating varieties (spore forming or sporogenous strains) but the cryET4 gene (SEQ ID NO:1) and cryET5 gene (SEQ ID NO:3) also have utility in asporogenous Bacillus strains, i.e., strains that produce the crystal protein without production of spores. It should be understood that references to "fermentation cultures" of B.t. strains containing the cryET4 gene (SEQ ID NO:1) or the cryET5 gene (SEQ ID NO:3) in this disclosure are intended to cover sporulated B.t. cultures, i.e., B.t. cultures containing the CryET1 crystal protein and spores, and sporogenous Bacillus strains that have produced crystal proteins during the vegetative stage, as well as asporogenous Bacillus strains containing the cryET4 gene (SEQ ID NO:1) or cryET5 (SEQ ID NO:3) gene in which the culture has reached the growth stage where the crystal protein is actually produced.

Mutants of B.t. strains harboring the cryET4 gene (SEQ ID NO:1) or cryET5 gene (SEQ ID NO:3) can be made by procedures well known in the art. For example, an asporogenous mutant can be obtained through ethylmethane sulfonate mutagenesis. Mutants can also be made using ultraviolet light and nitrosoguanidine by procedures that are well known to those skilled in the art. References in this specification to "mutants" of wild-type or recombinant B.t. strains harboring the cryET4 gene or cryET5 gene refer to those derivatives which are capable of producing toxin protein exhibiting insecticidal activity against lepidopteran insects, at least equivalent to the insecticidal activity of the parent strain.

The CryET4 protein (SEQ ID NO:2) is an insecticidal compound active against a large number of lepidopteran insects, particularly those described in Example 4. The CryET4 protein (SEQ ID NO:2) may be used as the active ingredient in insecticidal formulations useful for controlling lepidopteran insects.

The CryET5 protein (SEQ ID NO:4) is an insecticidal compound active against a large number of lepidopteran insects, particularly those described in Example 4. The CryET5 protein (SEQ ID NO:4) may be used as the active ingredient in insecticidal formulations useful for controlling lepidopteran insects.

Such insecticidal formulations or compositions typically contain agriculturally acceptable carriers or adjuvants in addition to the active ingredient and are prepared and used in a manner well known to those skilled in the art.

The CryET4 protein (SEQ ID NO:2) or CryET5 protein (SEQ ID NO:4) may be employed in insecticidal formulations in isolated or purified form, e.g., as the crystal protein itself. Alternatively, the CryET4 protein (SEQ ID NO:2) or CryET5 protein (SEQ ID NO:4) may be present in the recovered fermentation solids, obtained from culturing of a Bacillus strain, e.g., Bacillus thuringiensis or other microorganism host carrying the cryET4 gene (SEQ ID NO:1) or cryET5 gene (SEQ ID NO:3) and capable of producing the CryET4 or CryET5 protein. The CryET4 protein or CryET5 protein is thus associated with the B.t. bacterium which produced the protein, as an intimate mixture of crystal protein, cell debris and spores, if any, in the recovered fermentation solids. The recovered fermentation solids containing the CryET4 or CryET5 protein may be dried, if desired, prior to incorporation in the insecticidal formulation. Genetically engineered or transformed B.t. strains or other host microorganisms containing a recombinant plasmid that expresses the cloned cryET4 gene (SEQ ID NO:1) or cryET5 gene (SEQ ID NO:3), obtained by recombinant DNA procedures, may also be used. For construction of recombinant B.t. strains containing either the cryET4 gene or cryET5 gene, B.t. var. kurstaki strain EG10368 is a preferred host, and this B.t. strain is utilized in Example 2. B.t. strain EG10368 is a crystal-negative, toxin plasmid-free, naturally occurring mutant of B.t. strain HD73-26 (described in U.S. Pat. No. 5,080,897, issued to González, Jr. et al. on Jan. 14, 1992) that is highly transformable with recombinant plasmids, particularly those isolated from E. coli strains, e.g., DH5α.

The formulations or compositions of this invention containing the insecticidal CryET4 protein (SEQ ID NO:2) or CryET5 protein (SEQ ID NO:4) as the active component are applied at an insecticidally effective amount which will vary depending on such factors as, for example, the specific lepidopteran insects to be controlled, the specific plant or crop to be treated and the method of applying the insecticidally active compositions.

The insecticide compositions are made by formulating the insecticidally active component with the desired agriculturally acceptable carrier. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally acceptable carrier" covers all adjuvants, e.g., inert components, dispersants, surfactants, tackifiers, binders, etc. that are ordinarily used in insecticide formulation technology; these are well known to those skilled in insecticide formulation.

The formulations containing the CryET4 protein (SEQ ID NO:2) or CryET5 protein (SEQ ID NO:4) and one or more solid or liquid adjuvants are prepared in known manners, e.g., by homogeneously mixing, blending and/or grinding the insecticidally active CryET4 or CryET5 protein component with suitable adjuvants using conventional formulation techniques.

The insecticidal compositions of this invention are applied to the environment of the target lepidopteran insect, typically onto the foliage of the plant or crop to be protected, by conventional methods, preferably by spraying. Other application techniques, e.g., dusting, sprinkling, soaking, soil injection, seed coating, seedling coating or spraying, or the like, are also feasible and may be required for insects that cause root or stalk infestation. These application procedures are well known in the art.

The cryET4 gene (SEQ ID NO:1) or cryET5 gene (SEQ ID NO:3) may be introduced into a variety of microorganism hosts without undue experimentation, using procedures well known to those skilled in the art for transforming suitable hosts under conditions which allow for stable maintenance and expression of the cloned genes. Maniatis et al., *Molecular Cloning: A Laboratory Manual*, Cold Spring Harbor Laboratory Press, Cold Spring Harbor, N.Y. (1982). Suitable hosts that allow the cryET4 gene (SEQ ID NO:1) or cryET5 gene (SEQ ID NO:3) gene to be expressed and the CryET4 protein (SEQ ID NO:2) or CryET5 protein (SEQ ID NO:4) to be produced include *B.t.* and other Bacillus species such as *B. subtilis* or *B. megaterium*. A general method for the transformation of Bacillus strains is provided by Macaluso et al. in *J. Bacteriol.*, 173, pp. 1353–1356 (1991) and Mettus et al. in *Appl. Environ. Microbiol.*, 56, pp. 1128–1134 (1990). Genetically altered or engineered microorganisms containing the cryET4 gene (SEQ ID NO:1) or cryET5 gene (SEQ ID NO:3) can also contain other toxin genes present in the same microorganism; these genes could concurrently produce ICPs different from the CryET4 protein or CryET5 protein.

Plant-colonizing or root-colonizing microorganisms may also be employed as the host for the cryET4 gene (SEQ ID NO:1) or cryET5 gene (SEQ ID NO:3). Exemplary microorganism hosts for *B.t.* toxin genes include the plant-colonizing microbe *Clavibacter xyli* subsp. *cynodontis*, as described by Turner et al. in *Appl. Environ. Microbiol.*, 57, pp. 3522–3528, and root-colonizing pseudomonad strains, as described by Obukowicz et al. in *Gene*, 45, pp. 327–331 (1986). Procedures such as those described by Turner et al. (1991) supra, and Obukowicz et al. (1986), supra, are well known to those skilled in the art and available for introducing the cryET4 gene (SEQ ID NO:1) or cryET5 gene (SEQ ID NO:3) into such microorganism hosts under conditions which allow for stable maintenance and expression of the gene in the resulting transformants.

The transformants, i.e., host microorganisms that harbor a cloned gene in a recombinant plasmid, can be isolated in accordance with conventional methods, usually employing a selection technique, which allows growth of only those host microorganisms that contain a recombinant plasmid. The transformants then can be tested for insecticidal activity. These techniques are standard procedures well known to those skilled in the art.

Characteristics of particular interest in selecting a host cell for purposes of production include ease of introducing the gene into the host, availability of expression systems, efficiency of expression, stability of the CryET4 or CryET5 insecticidal protein in the host, and the presence of auxiliary genetic capabilities. The cellular host containing the insecticidal cryET4 gene (SEQ ID NO:1) or cryET5 gene (SEQ ID NO:3) may be grown in any convenient nutrient medium, where expression of the cryET4 gene or cryET5 gene is obtained and CryET4 protein (SEQ ID NO:2) or CryET5 protein (SEQ ID NO:4) produced, typically to sporulation. The sporulated cells containing the crystal protein may then be harvested in accordance with conventional methods, e.g., centrifugation or filtration.

The cryET4 gene (SEQ ID NO:1) or cryET5 gene (SEQ ID NO:3), particularly the toxin portion (N-terminal moiety) thereof, may also be incorporated into a plant which is capable of expressing the gene and producing CryET4 protein (SEQ ID NO:2) or CryET5 protein (SEQ ID NO:4), rendering the plant more resistant to insect attack. Genetic engineering of plants with the cryET4 gene (SEQ ID NO:1) or cryET5 gene (SEQ ID NO:3) may be accomplished by introducing the desired DNA containing the gene into plant tissues or cells, using DNA molecules of a variety of forms and origins that are well known to those skilled in plant genetic engineering. Examples of techniques for introducing DNA into plant tissue are disclosed in European Patent Application Publication No. 0 289 479, published Nov. 1, 1988, of Monsanto Company and by Perlak et al. in "Modification of the Coding Sequence Enhances Plant Expression of Insect Control Protein Genes," *Proc. Natl. Acad. Sci. USA*, 88, pp. 3324–3328 (1991).

DNA containing the cryET4 gene (SEQ ID NO:1) or cryET5 gene (SEQ ID NO:3) or a modified gene, operatively associated with a suitable plant promoter, e.g., CaMV35S, capable of effecting production of the CryET4 protein (SEQ ID NO:2) or CryET5 protein (SEQ ID NO:4), may be delivered into the plant cells or tissues directly by infectious plasmids, such as Ti, the plasmid from *Agrobacterium tumefaciens*, viruses or microorganisms like A. tumefaciens. Additionally, the use of lysosomes or liposomes, microinjection by mechanical methods and by other techniques familiar to those skilled in plant genetic engineering may be used.

The basic methods employed in the construction and evaluation of the recombinant plasmids and recombinant microorganism hosts described in this specification are generally well know to those proficient in the art of molecular cloning. Descriptions of these general laboratory procedures and definitions of nomenclature may be found in Maniatis et al., *Molecular Cloning: A Laboratory Manual*, Cold Spring Harbor Laboratory Press, Cold Spring Harbor, N.Y. (1982) and in a subsequent edition by Sambrook et al. (1989).

The characteristics of the CryET4 protein (SEQ ID NO:2) and CryET5 protein (SEQ ID NO:4), sequencing of the cryET4 gene (SEQ ID NO:1) and cryET5 gene (SEQ ID NO:3), comparison of sequence data to known B.t. toxin genes and insecticidal activity of the CryET4 and CryET5 proteins are described in the following specific, non-limiting examples.

EXAMPLE 1

Characterization of B.t. EG5847

B.t. strain EG5847 is a wild-type isolate, identified by visual examination of the colony as exhibiting a unique crystal morphology, and was isolated as a colony from maize dust. The colony contained endospores and bipyramidal and flat, diamond-shaped crystalline inclusions. Subsequent insect bioassay of this wild-type B.t. strain confirmed its insecticidal activity towards Lepidopteran insects.

The complement of native plasmids contained within isolated B.t. EG5847 was determined by modified Eckhardt agarose gel electrophoresis as described by González, Jr. et al., in *Proc. Natl. Acad. Sci. USA*, 79, pp. 6951–6955 (1982). The results, as shown in FIG. 3, revealed the presence of 5, 8, 12, 18 and 110 MDa plasmids. This pattern of native plasmids did not correspond to patterns typical of known serovars (Carlton and González, pp. 246–252, in *Molecular Biology of Microbial Differentiation*, J. A. Hoch and P. Setlow, ed., American Society for Microbiology, Washington, D.C. (1985)).

Wild-type B.t. strain EG5847 was grown for five days at 25° C. in DSM medium (described by Donovan et al. in *Appl. Environm. Microbiol.*, 58, pp. 3921–3927 (1992)) until sporulation and cell lysis had occurred. Recombinant B.t. strains EG7279 (Example 2), containing the cryET4 gene, and EG7283 (Example 2), containing the cryET5 gene, were grown in DSM medium containing 3 µg of chloramphenicol per ml in a similar manner. Fermentation solids containing spores and crystal proteins were isolated by centrifugation. Crystal proteins were purified from the spores and cell debris by sucrose density gradient centrifugation (described by Koller et al. in *Biochem. Biophys. Res. Communic.*, 184, pp. 692–699 (1992)). Aliquots of the washed crystals were solubilized by heating in Laemmli buffer (10% (w/w) glycerol, 5% (w/w) 2-mercaptoethanol, 1% (w/v) SDS, 0.188M Tris HCl pH 6.8, 0.01% (v/v) bromphenol blue) at 100° C. for 5 minutes. The solubilized crystal proteins were size fractionated by SDS-polyacrylamide gel electrophoresis. After size fractionation, the proteins were visualized by staining with Coomassie Blue R-250 dye.

FIG. 4 shows the results of these protein size fractionation analyses where lane 1 is a molecular mass size standard, lane 2 is B.t. strain EG5847, lane 3 is B.t. strain EG2729 and lane 4 is B.t. strain EG7283. The numbers on the left side indicate the apparent molecular masses, in kilodaltons (kDa), of the crystal proteins synthesized by the B.t. strains. As shown in lane 3, a crystal protein having a mass of approximately 130 kDa was observed from EG7279. As shown in lane 4 for EG7283, a crystal protein having a mass of approximately 130 kDa was produced. The wild type strain EG5847 exhibited a large protein band of approximately 130 kDa. The observed masses of the crystal proteins are in agreement with the masses predicted from the DNA sequences obtained in Example 3.

EXAMPLE 2

Cloning of the cryET4 and cryET5 Genes

Genomic DNA was isolated from B.t. strain EG5847 and then digested with HindIII. cryI-like genes were identified by Southern blotting (described by Southern, *J. Mol. Biol.* 98, pp. 503–517 (1975)). A radiolabelled 700 bp EcoR1 fragment of the cryIA(a) gene (described by Schnepf et al., *J. Biol. Chem.*, 260, pp. 6264–6272 (1985)) was used as a hybridization probe to identify cryI-like genes containing HindIII restriction fragments of EG5847 DNA. The 700 bp cryIA (a) fragment hybridized to several HindIII restriction fragments of EG5847 DNA including fragments of approximately 5.0 kb and 4.7 kb.

The 5.0 kb and 4.7 kb cryIA(a)-hybridizing HindIII restriction fragments of B.t. strain EG5847 were cloned as follows. DNA fragments of approximately 4–8 kb from HindIII digests of EG5847 genomic DNA were purified by agarose gel electrophoresis and electroelution. These fragments were ligated to the E. coli plasmid vector pUC18 and the ligation mixture was then used to transform E. coli. Ampicillin-resistant E. coli colonies were blotted to nitrocellulose filters (Grunstein et al., *Proc. Natl. Acad. Sci. USA* 72, pp. 3961–3965 (1975)). The filters were probed with the radiolabelled 700 bp cryIA(a) gene fragment. Two positive colonies, designated as E. coli strains EG7286 and EG7287, were identified and were selected for further analysis.

HindIII digestion of a plasmid, designated pEG291, isolated from E. coli strain EG7286 revealed a HindIII insert fragment 5.0 kb in size in pUC18. The restriction map of plasmid pEG291 is shown in FIG. 5A.

An E. coli/B. thuringiensis shuttle vector containing the 5.0 kb HindIII fragment was constructed by ligating BamHI digested Bacillus plasmid pNN101 (Norton et al., *Plasmid*, 13, pp. 211–214 (1985)) into the unique BamHI site of pEG291 (FIG. 5B). The resulting plasmid, designated pEG1108 (FIG. 5B), contains a full length open reading frame which has been designated as the cryET4 gene (SEQ ID NO:1).

E. coli strain EG7287 contained a plasmid, designated pEG292, which had a 4.7 kb HindIII insert in pUC18. DNA sequencing as described in Example 3 indicated that an open reading frame present in the 4.7 kb insert was truncated at its 3'-end (FIG. 6A). The truncated portion was isolated using a synthetic oligonucleotide having the sequence 5'-AAGTTTCGCATCCATCGATG-3' (SEQ ID NO:5). The oligonucleotide, designated WD162, was homologous to nucleotides 2253 to 2272 of the open reading frame identified in plasmid pEG292. Southern blot analyses as described above indicated that WD162 (SEQ ID NO:5) hybridized to a 3.2 kb HincII restriction fragment of EG5847 DNA. Radiolabelled WD162 was then used in colony blot experiments as described above to probe E. coli cells that contained a plasmid library consisting of size-selected HincII restriction fragments of EG5847 DNA. Several E. coli colonies hybridized with WD162 and one colony, designated E. coli strain EG7288, was selected for further analysis.

HincII restriction analysis of a recombinant plasmid, designated pEG300, isolated from E. coli EG7288, indicated that a 3.9 kb HincII fragment was present in pUC18. DNA sequencing as described below showed that pEG300 contained an open reading frame truncated at its 5'-end by the HincII cleavage site (FIG. 6B).

The full length open reading frame was constructed by excising a 2.6 kb XbaI-BsmI fragment containing the 5' portion of the open reading frame from plasmid pEG292 and inserting the fragment into the XbaI-BsmI restriction sites of plasmid pEG300 (FIG. 6A and 6B). The resulting plasmid, designated pEG1110 (FIG. 6C), contains a full length open reading frame which has been designated as the cryET5 gene (SEQ ID NO:3).

An E. coli/B. thuringiensis expression vector containing the full length open reading frame of the cryET5 gene was constructed by ligating XbaI digested Bacillus plasmid pNN101 (Norton, supra) into the unique XbaI site of plasmid pEG1110 (FIG. 6D). The resulting construct was designated plasmid pEG1111.

Plasmids pEG1108 and pEG1111 are capable of replicating in both E. coli and B.t. The plasmids were transformed by electroporation (Macaluso et al., J. Bacteriol., 173, pp. 1353–1356 (1991)) into the acrystalliferous B.t. strain EG10368 resulting in B.t. strains EG7279(PEG1108) and EG7283(pEG1111), respectively containing the cryET4 and cryET5 genes. Both of these B.t. strains are capable of expressing their respective protein toxin genes, as described in Example 4.

EXAMPLE 3

Sequencing of the cryET4 and cryET5 Genes

The complete DNA sequence of the cryET4 gene was determined using plasmid pEG291 (Example 2). Plasmid pEG291 was sequenced by standard methods (Sanger et al., Proc. Natl. Acad. Sci. USA, 74, pp. 5463–5467 (1977)). The DNA sequences of the appropriate subclones of the 5.0 kb HindIII fragment were joined to give a continuous sequence of 3713 nucleotides which is shown in FIG. 1 and is designated as SEQ ID NO:1. Inspection of the sequence revealed an open reading frame beginning at position 99 and extending to position 3602 (including the stop codon). The gene has been designated cryET4. The deduced 1167 amino acid sequence of the gene product is shown in FIG. 1 and is designated as SEQ ID NO:2. The mass of the CryET4 protein (SEQ ID NO:2) encoded by the cryET4 gene (SEQ ID NO:1), as deduced from the open reading frame, is 132,774 Da. Among CryI-type protein toxins reported in the literature, the CryIA(a) protein appears to be most closely related to the CryET4 protein. CryET4 exhibits 69% amino acid homology with CryIA(a).

The complete DNA sequence of the cryET5 gene (SEQ ID NO:3) was determined by the Sanger method as described above. Subcloned gene fragments from pEG292, pEG300 and pEG1110 were sequenced. The DNA sequences of the subcloned fragments were joined to give a continuous sequence of 3,934 nucleotides which is shown in FIG. 2 and is designated as SEQ ID NO:3. Inspection of the sequence revealed an open reading frame beginning at position 67 and extending to position 3756 (including the stop codon). The gene has been designated cryET5. The deduced 1229 amino acid sequence of the gene product encoded by the cryET5 gene (SEQ ID NO:3) is shown in FIG. 2 and is designated as SEQ ID NO:4. The mass of the CryET5 protein (SEQ ID NO:4) encoded by the cryET5 gene (SEQ ID NO:3), as deduced from the open reading frame, is 139,783 Da. Among CryI-type proteins reported in the literature, the CryIB protein appears to be most closely related to the CryET5 protein. CryET5 exhibits 83% amino acid homology with CryIB.

EXAMPLE 4

Insecticidal Activity of Recombinant Strains Harboring cryET4 and cryET5 Genes $PLC_{50}$ values of purified CryET4 and CryET5 crystal proteins were determined against lepidopteran insects, and these are listed in Tables 1 and 2, respectively. The $PLC_{50}$ dose is that amount of insecticidal crystal protein (ICP) which killed half of the insects tested, i.e., the median lethal concentration. CryET4 and CryET5 crystal proteins were isolated from B.t. strains EG7279 and EG7283, respectively, (described in Example 2) by sucrose density gradient centrifugation as described above. The amount of crystal protein recovered from the gradients was quantified by the Bradford protein assay (Bradford, Anal. Biochem., 72, p. 248 (1976)) after solubilization of the recovered crystal proteins with base and a reducing agent. Known amounts of purified crystals were diluted in 0.005% Triton® X-100 (v/v). Aliquots of eight two-fold serial dilutions (50 μl) were applied to the surfaces of 32 wells (1.8 cm² surface area) containing insect diet and dried for 1 hour at 30° C. A general purpose Noctuidae artificial diet (E. G. King et al., Handbook of Insect Rearing, Vol. 2, P. Singh and R. F. Moore (eds.), pp. 323–328, Elsevier Science Publishers B.V., Amsterdam (1985)) was used for Trichoplusia ni, Ostrinia nubilalis and Heliothis virescens. Other standard diets were used for the other lepidopteran insects tested. One neonate larva (third-instar larva in the case of P. xylostella) was added to each well, and the wells were incubated at 30° C. Mortality was recorded after seven days.

The insecticidal activity of CryET4 protein was compared with the activity of CryIA(a) protein (Schnepf et al., J. Biol. Chem., 260, pp. 6264–6272 (1985)). CryET4 exhibits a 69% amino acid sequence homology with CryIA(a). The results are presented in Table 1.

TABLE 1

| | $PLC_{50}$ Bioassay Activity of Purified CryET4 | |
| | $PLC_{50}$ (ng ICP/well) | |
| Insect Species | CryET4 | CryIA(a) |
| --- | --- | --- |
| Heliothis virescens | 593 (493–711)** | 94 (76–113) |
| Helicoverpa zea | 1,290 (1,046–1,599) | 3,725 (3,004–4,551) |
| Lymantria dispar | 9,929 (5,767–26,039) | 185 (138–243) |
| Ostrinia nubilalis | 197 (121–299) | 34 (27–42) |
| Pseudoplusia includens | 33 (29–37) | 14 (12–16) |
| Plutella xylostella | 30 (22–41) | 12 (10–14) |
| Javelin ®*-resistant P. xylostella | 4,758 (3,135–6,897) | >50,000 |
| Spodoptera exigua | 1,748 (1,286–2,591) | >20,000 |
| Spodoptera frugiperda | 1,161 (555–2,115) | >10,000 |
| Trichoplusia ni | 62 (53–74) | 80 (54–113) |

*Javelin is a commercial B.t. bioinsecticide.
**Range in parentheses indicates 95% confidence level.

The $PLC_{50}$ results in Table 1 indicate that the CryET4 protein (SEQ ID NO:2) exhibits good insecticidal activity to a broad spectrum of lepidopteran insects.

The results show that the CryET4 protein is more toxic than CryIA(a) against Helicoverpa zea (corn earworm/bollworm), Javelin®-resistant Plutella xylostella (diamondback moth), Spodoptera exigua (beet armyworm) and Spodoptera frugiperda (fall armyworm).

Particularly noteworthy is the very good activity against Spodoptera exigua (beet armyworm), an insect pest that not only is not susceptible to CryIA(a), but also is recalcitrant to most B.t. toxin proteins, and very good activity against Spodoptera frugiperda (fall armyworm), another recalcitrant insect pest. Activity against Pseudoplusia includens (soybean looper), Plutella xylostella (diamondback moth) and Trichoplusia ni (cabbage looper) was also good, comparable to that exhibited by CryIA(a).

Insect bioassay tests with CryET4 protein were also carried out against another lepidopteran insect, *Agrotis ipsilon* (black cutworm), which was found not to be susceptible to control with CryET4.

The insecticidal activity of CryET5 protein was compared with the activity of CryIB protein (Brizzard et al., *Nucleic Acids Res.* 16, 2723–2724 (1988)). CryET5 exhibits an 83% amino acid sequence homology with CryIB. Dilutions of purified CryET5 crystals were prepared in 0.005% Triton® X-100. Aliquots of appropriate dilutions (50 μl) were applied to the surfaces of 32 wells and assayed as indicated above. The results are presented in Table 2.

TABLE 2

$PLC_{50}$ Bioassay Activity of Purified CryET5

| Insect Species | $PLC_{50}$ (ng ICP/well) | |
|---|---|---|
| | CryET5 | CryIB |
| Lymantria dispar | 880 (555–1,397)** | 3,580 (1,293–20,123) |
| Ostrinia nubilalis | 32 (29–37) | 83 (51–123) |
| Pseudoplusia includens | 555 (437–646) | 52 (44–61) |
| Plutella xylostella | 157 (127–193) | 27 (23–32) |
| Javelin ®*-resistant P. xylostella | 47 (23–80) | 43 (35–55) |
| Spodoptera frugiperda | 2,812 (1,831–4,514) | >10,000 |
| Trichoplusia ni | 22 (19–27) | 205 (176–241) |

*Javelin is a commercial B.t. bioinsecticide.
**Range in parentheses indicates 95% confidence level.

The $PLC_{50}$ results in Table 2 indicate that the CryET5 protein (SEQ ID NO:4) exhibits good insecticidal activity to a broad spectrum of lepidopteran insects.

The results show that the CryET5 protein is more toxic than CryIB against Spodoptera frugiperda (fall armyworm) and *Trichoplusia ni* (cabbage looper). The CryET5 protein and CryIB protein both exhibited excellent insecticidal activity against Javelin®-resistant *Plutella xylostella* (diamondback moth), a *B.t.*-resistant insect pest that is not susceptible to CryIA-type toxin proteins, and to *Ostrinia nubilalis* (European corn borer).

Insect bioassay tests with CryET5 protein were also carried out against a few other lepidopteran insects, but these were found not to be susceptible to control with CryET5: *Agrotis ipsilon* (black cutworm), *Heliothis virescens* (tobacco budworm), *Helicoverpa zea* (corn earworm/bollworm) and *Spodoptera exigua* (beet armyworm).

The present invention may be embodied in other specific forms without departing from the spirit or essential attributes thereof and, accordingly, reference should be made to the appended claims, rather than to the foregoing specification as indicating the scope of the invention.

---

We claim:

1. A biologically pure culture of a *Bacillus thuringiensis* bacterium deposited with the NRRL having accession number NRRL B-21110 and being designated as strain EG5847.

2. A biologically pure culture of a *Bacillus thuringiensis* bacterium deposited with the NRRL having accession number NRRL B-21125 and being designated as strain EG10368.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 3713 base pairs
( B ) TYPE: nucleic acid
( C ) STRANDEDNESS: double
( D ) TOPOLOGY: circular ( i i ) MOLECULE TYPE: DNA (genomic)

( i x ) FEATURE:
( A ) NAME/KEY: CDS
( B ) LOCATION: 99..3602

( x i ) SEQUENCE DESCRIPTION: SEQ ID NO:1:

```
AAATTCATAA TATGAATCAT ACGTTTTAAA GTGTTGTGAA GAAAAGAGAA TTGATCTTTA         60

GAATTTTTTT ATTTTAACCA AAGAGAAAGG GGTAACTT ATG GAG ATA AAT AAT           113
                                            Met Glu Ile Asn Asn
                                            1               5

CAG AAG CAA TGC ATA CCA TAT AAT TGC TTA AGT AAT CCT GAG GAA GTA         161
Gln Lys Gln Cys Ile Pro Tyr Asn Cys Leu Ser Asn Pro Glu Glu Val
            10                  15                  20

CTT TTG GAT GGG GAG AGG ATA TTA CCT GAT ATC GAT CCA CTC GAA GTT         209
Leu Leu Asp Gly Glu Arg Ile Leu Pro Asp Ile Asp Pro Leu Glu Val
        25                  30                  35

TCT TTG TCG CTT TTG CAA TTT CTT TTG AAT AAC TTT GTT CCA GGG GGA         257
Ser Leu Ser Leu Leu Gln Phe Leu Leu Asn Asn Phe Val Pro Gly Gly
    40                  45                  50
```

```
GGC  TTT  ATT  TCA  GGA  TTA  GTT  GAT  AAA  ATA  TGG  GGG  GCT  TTG  AGA  CCA        305
Gly  Phe  Ile  Ser  Gly  Leu  Val  Asp  Lys  Ile  Trp  Gly  Ala  Leu  Arg  Pro
     55                       60                      65

TCT  GAA  TGG  GAC  TTA  TTT  CTT  GCA  CAG  ATT  GAA  CGG  TTG  ATT  GAT  CAA        353
Ser  Glu  Trp  Asp  Leu  Phe  Leu  Ala  Gln  Ile  Glu  Arg  Leu  Ile  Asp  Gln
70                       75                       80                            85

AGA  ATA  GAA  GCA  ACA  GTA  AGA  GCA  AAA  GCA  ATC  ACT  GAA  TTA  GAA  GGA        401
Arg  Ile  Glu  Ala  Thr  Val  Arg  Ala  Lys  Ala  Ile  Thr  Glu  Leu  Glu  Gly
                    90                       95                            100

TTA  GGG  AGA  AAT  TAT  CAA  ATA  TAC  GCT  GAA  GCA  TTT  AAA  GAA  TGG  GAA        449
Leu  Gly  Arg  Asn  Tyr  Gln  Ile  Tyr  Ala  Glu  Ala  Phe  Lys  Glu  Trp  Glu
                    105                      110                 115

TCA  GAT  CCT  GAT  AAC  GAA  GCG  GCT  AAA  AGT  AGA  GTA  ATT  GAT  CGC  TTT        497
Ser  Asp  Pro  Asp  Asn  Glu  Ala  Ala  Lys  Ser  Arg  Val  Ile  Asp  Arg  Phe
          120                      125                      130

CGT  ATA  CTT  GAT  GGT  CTA  ATT  GAA  GCA  AAT  ATC  CCT  TCA  TTT  CGG  ATA        545
Arg  Ile  Leu  Asp  Gly  Leu  Ile  Glu  Ala  Asn  Ile  Pro  Ser  Phe  Arg  Ile
     135                      140                      145

ATT  GGA  TTT  GAA  GTG  CCA  CTT  TTA  TCG  GTT  TAT  GTT  CAA  GCA  GCT  AAT        593
Ile  Gly  Phe  Glu  Val  Pro  Leu  Leu  Ser  Val  Tyr  Val  Gln  Ala  Ala  Asn
150                      155                      160                      165

CTA  CAT  CTC  GCT  CTA  TTG  AGA  GAT  TCT  GTT  ATT  TTT  GGA  GAG  AGA  TGG        641
Leu  His  Leu  Ala  Leu  Leu  Arg  Asp  Ser  Val  Ile  Phe  Gly  Glu  Arg  Trp
                    170                      175                      180

GGA  TTG  ACG  ACA  AAA  AAT  GTC  AAT  GAT  ATC  TAT  AAT  AGA  CAA  ATT  AGA        689
Gly  Leu  Thr  Thr  Lys  Asn  Val  Asn  Asp  Ile  Tyr  Asn  Arg  Gln  Ile  Arg
               185                      190                      195

GAA  ATT  CAT  GAA  TAT  AGC  AAT  CAT  TGC  GTA  GAT  ACG  TAT  AAC  ACA  GAA        737
Glu  Ile  His  Glu  Tyr  Ser  Asn  His  Cys  Val  Asp  Thr  Tyr  Asn  Thr  Glu
               200                      205                      210

CTA  GAA  CGT  CTA  GGG  TTT  AGA  TCT  ATA  GCG  CAG  TGG  AGA  ATA  TAT  AAT        785
Leu  Glu  Arg  Leu  Gly  Phe  Arg  Ser  Ile  Ala  Gln  Trp  Arg  Ile  Tyr  Asn
     215                      220                      225

CAG  TTT  AGA  AGA  GAA  CTA  ACA  CTA  ACT  GTA  TTA  GAT  ATT  GTC  GCT  CTT        833
Gln  Phe  Arg  Arg  Glu  Leu  Thr  Leu  Thr  Val  Leu  Asp  Ile  Val  Ala  Leu
230                      235                      240                      245

TTC  CCG  AAC  TAT  GAC  AGT  AGA  CTG  TAT  CCG  ATC  CAA  ACT  TTT  TCT  CAA        881
Phe  Pro  Asn  Tyr  Asp  Ser  Arg  Leu  Tyr  Pro  Ile  Gln  Thr  Phe  Ser  Gln
                    250                      255                      260

TTG  ACA  AGA  GAA  ATT  GTT  ACA  TCC  CCA  GTA  AGC  GAA  TTT  TAT  TAT  GGT        929
Leu  Thr  Arg  Glu  Ile  Val  Thr  Ser  Pro  Val  Ser  Glu  Phe  Tyr  Tyr  Gly
               265                      270                      275

GTT  ATT  AAT  AGT  GGT  AAT  ATA  ATT  GGT  ACT  CTT  ACT  GAA  CAG  CAG  ATA        977
Val  Ile  Asn  Ser  Gly  Asn  Ile  Ile  Gly  Thr  Leu  Thr  Glu  Gln  Gln  Ile
          280                      285                      290

AGG  CGA  CCA  CAT  CTT  ATG  GAC  TTC  TTT  AAC  TCC  ATG  ATC  ATG  TAT  ACA       1025
Arg  Arg  Pro  His  Leu  Met  Asp  Phe  Phe  Asn  Ser  Met  Ile  Met  Tyr  Thr
     295                      300                      305

TCA  GAT  AAT  AGA  CGG  GAA  CAT  TAT  TGG  TCA  GGA  CTT  GAA  ATG  ACG  GCT       1073
Ser  Asp  Asn  Arg  Arg  Glu  His  Tyr  Trp  Ser  Gly  Leu  Glu  Met  Thr  Ala
310                      315                      320                      325

TAT  TTT  ACA  GGA  TTT  GCA  GGA  GCT  CAA  GTG  TCA  TTC  CCT  TTA  GTC  GGG       1121
Tyr  Phe  Thr  Gly  Phe  Ala  Gly  Ala  Gln  Val  Ser  Phe  Pro  Leu  Val  Gly
                    330                      335                      340

ACT  AGA  GGG  GAG  TCA  GCT  CCA  CCA  TTA  ACT  GTT  AGA  AGT  GTT  AAT  GAT       1169
Thr  Arg  Gly  Glu  Ser  Ala  Pro  Pro  Leu  Thr  Val  Arg  Ser  Val  Asn  Asp
               345                      350                      355

GGA  ATT  TAT  AGA  ATA  TTA  TCG  GCA  CCG  TTT  TAT  TCA  GCG  CCT  TTT  CTA       1217
Gly  Ile  Tyr  Arg  Ile  Leu  Ser  Ala  Pro  Phe  Tyr  Ser  Ala  Pro  Phe  Leu
          360                      365                      370
```

| | | | | | | | | | | | | | | | |
|---|---|---|---|---|---|---|---|---|---|---|---|---|---|---|---|
| GGC | ACC | ATT | GTA | TTG | GGA | AGT | CGT | GGA | GAA | AAA | TTT | GAT | TTT | GCG | CTT | 1265
| Gly | Thr | Ile | Val | Leu | Gly | Ser | Arg | Gly | Glu | Lys | Phe | Asp | Phe | Ala | Leu |
| | 375 | | | | 380 | | | | | 385 | | | | | |
| AAT | AAT | ATT | TCA | CCT | CCG | CCA | TCT | ACA | ATA | TAC | AGA | CAT | CCT | GGA | ACA | 1313
| Asn | Asn | Ile | Ser | Pro | Pro | Pro | Ser | Thr | Ile | Tyr | Arg | His | Pro | Gly | Thr |
| 390 | | | | | 395 | | | | | 400 | | | | | 405 |
| GTA | GAT | TCA | CTA | GTC | AGT | ATA | CCG | CCA | CAG | GAT | AAT | AGC | GTA | CCA | CCG | 1361
| Val | Asp | Ser | Leu | Val | Ser | Ile | Pro | Pro | Gln | Asp | Asn | Ser | Val | Pro | Pro |
| | | | | 410 | | | | | 415 | | | | | 420 | |
| CAC | AGG | GGA | TCT | AGT | CAT | CGA | TTA | AGT | CAT | GTT | ACA | ATG | CGC | GCA | AGT | 1409
| His | Arg | Gly | Ser | Ser | His | Arg | Leu | Ser | His | Val | Thr | Met | Arg | Ala | Ser |
| | | | 425 | | | | | 430 | | | | | 435 | | |
| TCC | CCT | ATA | TTC | CAT | TGG | ACG | CAT | CGC | AGC | GCA | ACC | ACT | ACA | AAT | ACA | 1457
| Ser | Pro | Ile | Phe | His | Trp | Thr | His | Arg | Ser | Ala | Thr | Thr | Thr | Asn | Thr |
| | | 440 | | | | | 445 | | | | | 450 | | | |
| ATT | AAT | CCA | AAT | GCT | ATT | ATC | CAA | ATA | CCA | CTA | GTA | AAA | GCA | TTT | AAC | 1505
| Ile | Asn | Pro | Asn | Ala | Ile | Ile | Gln | Ile | Pro | Leu | Val | Lys | Ala | Phe | Asn |
| | 455 | | | | | 460 | | | | | 465 | | | | |
| CTT | CAT | TCA | GGT | GCC | ACT | GTT | GTT | AGA | GGA | CCA | GGG | TTT | ACA | GGT | GGT | 1553
| Leu | His | Ser | Gly | Ala | Thr | Val | Val | Arg | Gly | Pro | Gly | Phe | Thr | Gly | Gly |
| 470 | | | | | 475 | | | | | 480 | | | | | 485 |
| GAT | ATC | CTT | CGA | AGA | ACG | AAT | ACT | GGC | ACA | TTT | GCA | GAT | ATG | AGA | GTA | 1601
| Asp | Ile | Leu | Arg | Arg | Thr | Asn | Thr | Gly | Thr | Phe | Ala | Asp | Met | Arg | Val |
| | | | | 490 | | | | | 495 | | | | | 500 | |
| AAT | ATT | ACT | GGG | CCA | TTA | TCC | CAA | AGA | TAT | CGT | GTA | AGA | ATT | CGC | TAT | 1649
| Asn | Ile | Thr | Gly | Pro | Leu | Ser | Gln | Arg | Tyr | Arg | Val | Arg | Ile | Arg | Tyr |
| | | | 505 | | | | | 510 | | | | | 515 | | |
| GCT | TCT | ACG | ACA | GAT | TTA | CAA | TTT | TTC | ACG | AGA | ATC | AAT | GGA | ACT | TCT | 1697
| Ala | Ser | Thr | Thr | Asp | Leu | Gln | Phe | Phe | Thr | Arg | Ile | Asn | Gly | Thr | Ser |
| | | 520 | | | | | 525 | | | | | 530 | | | |
| GTA | AAT | CAA | GGT | AAT | TTC | CAA | AGA | ACT | ATG | AAT | AGA | GGG | GAT | AAT | TTA | 1745
| Val | Asn | Gln | Gly | Asn | Phe | Gln | Arg | Thr | Met | Asn | Arg | Gly | Asp | Asn | Leu |
| | 535 | | | | | 540 | | | | | 545 | | | | |
| GAA | TCT | GGA | AAC | TTT | AGG | ACT | GCA | GGA | TTT | AGT | ACG | CCT | TTT | AGT | TTT | 1793
| Glu | Ser | Gly | Asn | Phe | Arg | Thr | Ala | Gly | Phe | Ser | Thr | Pro | Phe | Ser | Phe |
| 550 | | | | | 555 | | | | | 560 | | | | | 565 |
| TCA | AAT | GCG | CAA | AGT | ACA | TTC | ACA | TTG | GGT | ACT | CAG | GCT | TTT | TCA | AAT | 1841
| Ser | Asn | Ala | Gln | Ser | Thr | Phe | Thr | Leu | Gly | Thr | Gln | Ala | Phe | Ser | Asn |
| | | | | 570 | | | | | 575 | | | | | 580 | |
| CAG | GAA | GTT | TAT | ATA | GAT | CGA | ATT | GAA | TTT | GTC | CCG | GCA | GAA | GTA | ACA | 1889
| Gln | Glu | Val | Tyr | Ile | Asp | Arg | Ile | Glu | Phe | Val | Pro | Ala | Glu | Val | Thr |
| | | | 585 | | | | | 590 | | | | | 595 | | |
| TTC | GAG | GCA | GAA | TCT | GAT | TTA | GAA | AGA | GCG | CAA | AAG | GCG | GTG | AAT | GCC | 1937
| Phe | Glu | Ala | Glu | Ser | Asp | Leu | Glu | Arg | Ala | Gln | Lys | Ala | Val | Asn | Ala |
| | | 600 | | | | | 605 | | | | | 610 | | | |
| CTG | TTT | ACT | TCT | ACA | AAC | CAA | CTA | GGG | CTA | AAA | ACA | GAT | GTG | ACG | GAT | 1985
| Leu | Phe | Thr | Ser | Thr | Asn | Gln | Leu | Gly | Leu | Lys | Thr | Asp | Val | Thr | Asp |
| | 615 | | | | | 620 | | | | | 625 | | | | |
| TAT | CAG | ATT | GAT | CAA | GTG | TCC | AAT | TTA | GTA | GAA | TGT | TTA | TCA | GAT | GAA | 2033
| Tyr | Gln | Ile | Asp | Gln | Val | Ser | Asn | Leu | Val | Glu | Cys | Leu | Ser | Asp | Glu |
| 630 | | | | | 635 | | | | | 640 | | | | | 645 |
| TTT | TGT | CTG | GAT | GAA | AAG | AGA | GAA | TTG | TCC | GAG | AAA | GTC | AAA | CAT | GCA | 2081
| Phe | Cys | Leu | Asp | Glu | Lys | Arg | Glu | Leu | Ser | Glu | Lys | Val | Lys | His | Ala |
| | | | | 650 | | | | | 655 | | | | | 660 | |
| AAG | CGA | CTT | AGT | GAT | AAG | CGG | AAC | CTA | CTT | CAA | GAT | CCA | AAC | TTC | ACA | 2129
| Lys | Arg | Leu | Ser | Asp | Lys | Arg | Asn | Leu | Leu | Gln | Asp | Pro | Asn | Phe | Thr |
| | | | 665 | | | | | 670 | | | | | 675 | | |
| TCT | ATC | AAT | AGA | CAA | CTA | GAC | CGT | GGA | TGG | AGA | GGA | AGT | ACG | GAT | ATT | 2177
| Ser | Ile | Asn | Arg | Gln | Leu | Asp | Arg | Gly | Trp | Arg | Gly | Ser | Thr | Asp | Ile |
| | | 680 | | | | | 685 | | | | | 690 | | | |

| | | | | | | | | | | | | | | | | |
|---|---|---|---|---|---|---|---|---|---|---|---|---|---|---|---|---|
| ACC | ATC | CAA | GGA | GGA | AAT | GAC | GTA | TTC | AAA | GAG | AAT | TAC | GTC | ACA | CTA | 2225 |
| Thr | Ile | Gln | Gly | Gly | Asn | Asp | Val | Phe | Lys | Glu | Asn | Tyr | Val | Thr | Leu | |
| | 695 | | | | 700 | | | | | 705 | | | | | | |
| CCA | GGT | ACC | TTT | GAT | GAG | TGT | TAT | CCA | ACG | TAT | TTG | TAT | CAA | AAA | ATA | 2273 |
| Pro | Gly | Thr | Phe | Asp | Glu | Cys | Tyr | Pro | Thr | Tyr | Leu | Tyr | Gln | Lys | Ile | |
| 710 | | | | | 715 | | | | | 720 | | | | | 725 | |
| GAT | GAG | TCA | AAA | TTA | AAA | GCC | TAT | ACT | CGC | TAT | GAA | TTA | AGA | GGG | TAT | 2321 |
| Asp | Glu | Ser | Lys | Leu | Lys | Ala | Tyr | Thr | Arg | Tyr | Glu | Leu | Arg | Gly | Tyr | |
| | | | | 730 | | | | | 735 | | | | | 740 | | |
| ATT | GAA | GAT | AGT | CAA | GAT | TTA | GAA | GTC | TAT | TTG | ATT | CGT | TAC | AAT | GCG | 2369 |
| Ile | Glu | Asp | Ser | Gln | Asp | Leu | Glu | Val | Tyr | Leu | Ile | Arg | Tyr | Asn | Ala | |
| | | | 745 | | | | | 750 | | | | | 755 | | | |
| AAA | CAT | GAA | ACA | GTA | AAT | GTT | CCC | GGT | ACA | GGG | TCC | TTA | TGG | CCG | CTT | 2417 |
| Lys | His | Glu | Thr | Val | Asn | Val | Pro | Gly | Thr | Gly | Ser | Leu | Trp | Pro | Leu | |
| | | 760 | | | | | 765 | | | | | 770 | | | | |
| TCA | GTC | GAA | AGC | CCA | ATC | GGA | AGG | TGC | GGA | GAA | CCG | AAT | CGA | TGT | GTG | 2465 |
| Ser | Val | Glu | Ser | Pro | Ile | Gly | Arg | Cys | Gly | Glu | Pro | Asn | Arg | Cys | Val | |
| | 775 | | | | | 780 | | | | | 785 | | | | | |
| CCA | CAT | ATT | GAA | TGG | AAT | CCT | GAT | TTA | GAT | TGT | TCG | TGT | AGG | GAT | GGG | 2513 |
| Pro | His | Ile | Glu | Trp | Asn | Pro | Asp | Leu | Asp | Cys | Ser | Cys | Arg | Asp | Gly | |
| 790 | | | | | 795 | | | | | 800 | | | | | 805 | |
| GAG | AAG | TGT | GCC | CAT | CAT | TCG | CAT | CAT | TTC | TCT | CTA | GAT | ATT | GAT | GTT | 2561 |
| Glu | Lys | Cys | Ala | His | His | Ser | His | His | Phe | Ser | Leu | Asp | Ile | Asp | Val | |
| | | | | 810 | | | | | 815 | | | | | 820 | | |
| GGA | TGT | ACA | GAC | CTA | AAT | GAG | GAC | CTA | GGT | GTA | TGG | GTG | ATC | TTT | AAG | 2609 |
| Gly | Cys | Thr | Asp | Leu | Asn | Glu | Asp | Leu | Gly | Val | Trp | Val | Ile | Phe | Lys | |
| | | | 825 | | | | | 830 | | | | | 835 | | | |
| ATT | AAA | ACG | CAG | GAT | GGC | CAT | GCA | AGA | TTA | GGA | AAT | CTA | GAG | TTT | CTC | 2657 |
| Ile | Lys | Thr | Gln | Asp | Gly | His | Ala | Arg | Leu | Gly | Asn | Leu | Glu | Phe | Leu | |
| | | 840 | | | | | 845 | | | | | 850 | | | | |
| GAA | GAG | AAA | CCA | TTG | TTA | GGA | GAA | GCG | TTA | GCT | CGT | GTG | AAA | AGA | GCG | 2705 |
| Glu | Glu | Lys | Pro | Leu | Leu | Gly | Glu | Ala | Leu | Ala | Arg | Val | Lys | Arg | Ala | |
| | 855 | | | | | 860 | | | | | 865 | | | | | |
| GAG | AAA | AAA | TGG | AGA | GAC | AAA | CGC | GAA | CAA | TTG | CAG | TTT | GAA | ACG | AAT | 2753 |
| Glu | Lys | Lys | Trp | Arg | Asp | Lys | Arg | Glu | Gln | Leu | Gln | Phe | Glu | Thr | Asn | |
| 870 | | | | | 875 | | | | | 880 | | | | | 885 | |
| ATC | GTT | TAC | AAA | GAG | GCA | AAA | GAA | TCT | GTA | GAT | GCT | TTA | TTC | GTA | GAT | 2801 |
| Ile | Val | Tyr | Lys | Glu | Ala | Lys | Glu | Ser | Val | Asp | Ala | Leu | Phe | Val | Asp | |
| | | | | 890 | | | | | 895 | | | | | 900 | | |
| TCT | CAC | TAT | AAT | AGA | TTA | CAA | GCG | GAT | ACG | AAC | ATT | ACG | ATG | ATT | CAT | 2849 |
| Ser | His | Tyr | Asn | Arg | Leu | Gln | Ala | Asp | Thr | Asn | Ile | Thr | Met | Ile | His | |
| | | | 905 | | | | | 910 | | | | | 915 | | | |
| GCG | GCA | GAT | AAA | CGC | GTT | CAT | CGA | ATC | CGA | GAG | GCT | TAT | CTT | CCG | GAA | 2897 |
| Ala | Ala | Asp | Lys | Arg | Val | His | Arg | Ile | Arg | Glu | Ala | Tyr | Leu | Pro | Glu | |
| | | 920 | | | | | 925 | | | | | 930 | | | | |
| TTA | TCC | GTT | ATC | CCA | GGT | GTA | AAT | GCG | GAC | ATT | TTT | GAA | GAA | TTA | GAA | 2945 |
| Leu | Ser | Val | Ile | Pro | Gly | Val | Asn | Ala | Asp | Ile | Phe | Glu | Glu | Leu | Glu | |
| | 935 | | | | | 940 | | | | | 945 | | | | | |
| GGT | CTT | ATT | TTC | ACT | GCA | TTC | TCC | CTA | TAT | GAT | GCG | AGA | AAT | ATC | ATT | 2993 |
| Gly | Leu | Ile | Phe | Thr | Ala | Phe | Ser | Leu | Tyr | Asp | Ala | Arg | Asn | Ile | Ile | |
| 950 | | | | | 955 | | | | | 960 | | | | | 965 | |
| AAA | AAC | GGT | GAT | TTC | AAT | AAT | GGT | TTA | TCG | TGT | TGG | AAC | GTG | AAA | GGG | 3041 |
| Lys | Asn | Gly | Asp | Phe | Asn | Asn | Gly | Leu | Ser | Cys | Trp | Asn | Val | Lys | Gly | |
| | | | | 970 | | | | | 975 | | | | | 980 | | |
| CAT | GTA | GAT | ATA | CAA | CAG | AAT | GAT | CAT | CGT | TCT | GTC | CTC | GTT | GTC | CCG | 3089 |
| His | Val | Asp | Ile | Gln | Gln | Asn | Asp | His | Arg | Ser | Val | Leu | Val | Val | Pro | |
| | | | 985 | | | | | 990 | | | | | 995 | | | |
| GAA | TGG | GAA | TCA | GAG | GTA | TCA | CAA | GAA | GTC | CGC | GTA | TGT | CCA | GGT | CGT | 3137 |
| Glu | Trp | Glu | Ser | Glu | Val | Ser | Gln | Glu | Val | Arg | Val | Cys | Pro | Gly | Arg | |
| | | 1000 | | | | | 1005 | | | | | 1010 | | | | |

```
GGC TAT ATT CTT CGT GTC ACA GCG TAC AAA GAG GGC TAC GGA GAA GGA    3185
Gly Tyr Ile Leu Arg Val Thr Ala Tyr Lys Glu Gly Tyr Gly Glu Gly
    1015                1020                1025

TGC GTA ACG ATC CAT GAG ATC GAA GAC AAT ACA GAC GAA TTG AAG TTT    3233
Cys Val Thr Ile His Glu Ile Glu Asp Asn Thr Asp Glu Leu Lys Phe
1030                1035                1040                1045

AGT AAC TGC ATA GAA GAG GAA GTC TAT CCA ACG GAT ACA GGT AAT GAT    3281
Ser Asn Cys Ile Glu Glu Glu Val Tyr Pro Thr Asp Thr Gly Asn Asp
                1050                1055                1060

TAT ACT GCA CAC CAA GGT ACA ACA GGA TGC GCA GAT GCA TGT AAT TCC    3329
Tyr Thr Ala His Gln Gly Thr Thr Gly Cys Ala Asp Ala Cys Asn Ser
                1065                1070                1075

CGT AAT GTT GGA TAT GAG GAT GGA TAT GAA ATA AAT ACT ACA GCA TCT    3377
Arg Asn Val Gly Tyr Glu Asp Gly Tyr Glu Ile Asn Thr Thr Ala Ser
            1080                1085                1090

GTT AAT TAC AAA CCG ACT TAT GAA GAA GAA ATG TAT ACA GAT GTA CGA    3425
Val Asn Tyr Lys Pro Thr Tyr Glu Glu Glu Met Tyr Thr Asp Val Arg
    1095                1100                1105

AGA GAT AAT CAT TGT GAA TAT GAC AGA GGA TAT GGG AAC CAT ACA CCG    3473
Arg Asp Asn His Cys Glu Tyr Asp Arg Gly Tyr Gly Asn His Thr Pro
1110                1115                1120                1125

TTA CCA GCT GGT TAT GTA ACA AAA GAA TTA GAG TAC TTC CCT GAA ACA    3521
Leu Pro Ala Gly Tyr Val Thr Lys Glu Leu Glu Tyr Phe Pro Glu Thr
                1130                1135                1140

GAT ACA GTA TGG ATA GAG ATT GGA GAA ACG GAA GGA ACA TTC ATC GTA    3569
Asp Thr Val Trp Ile Glu Ile Gly Glu Thr Glu Gly Thr Phe Ile Val
                1145                1150                1155

GAT AGT GTG GAA TTA CTC CTC ATG GAG GAA  TAAGATTGTA CGAAATCGAC     3619
Asp Ser Val Glu Leu Leu Leu Met Glu Glu
                1160            1165

TTTAAATGGC TCATTCTAAA CAAAAAGTAG TCGTCTAATC TCTGTAACAA ATAGAAAAGT  3679

AAATATTTGT AGAAAAAAGA AAAAGGACAT TACT                              3713
```

( 2 ) INFORMATION FOR SEQ ID NO:2:

( i ) SEQUENCE CHARACTERISTICS:
            ( A ) LENGTH: 1167 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

```
Met Glu Ile Asn Asn Gln Lys Gln Cys Ile Pro Tyr Asn Cys Leu Ser
  1               5                  10                  15

Asn Pro Glu Glu Val Leu Leu Asp Gly Glu Arg Ile Leu Pro Asp Ile
                 20                  25                  30

Asp Pro Leu Glu Val Ser Leu Ser Leu Leu Gln Phe Leu Leu Asn Asn
             35                  40                  45

Phe Val Pro Gly Gly Gly Phe Ile Ser Gly Leu Val Asp Lys Ile Trp
         50                  55                  60

Gly Ala Leu Arg Pro Ser Glu Trp Asp Leu Phe Leu Ala Gln Ile Glu
 65                  70                  75                  80

Arg Leu Ile Asp Gln Arg Ile Glu Ala Thr Val Arg Ala Lys Ala Ile
                 85                  90                  95

Thr Glu Leu Glu Gly Leu Gly Arg Asn Tyr Gln Ile Tyr Ala Glu Ala
                100                 105                 110

Phe Lys Glu Trp Glu Ser Asp Pro Asp Asn Glu Ala Ala Lys Ser Arg
            115                 120                 125
```

```
Val  Ile  Asp  Arg  Phe  Arg  Ile  Leu  Asp  Gly  Leu  Ile  Glu  Ala  Asn  Ile
     130                 135                      140

Pro  Ser  Phe  Arg  Ile  Ile  Gly  Phe  Glu  Val  Pro  Leu  Leu  Ser  Val  Tyr
145                      150                 155                           160

Val  Gln  Ala  Ala  Asn  Leu  His  Leu  Ala  Leu  Leu  Arg  Asp  Ser  Val  Ile
               165                      170                           175

Phe  Gly  Glu  Arg  Trp  Gly  Leu  Thr  Thr  Lys  Asn  Val  Asn  Asp  Ile  Tyr
               180                 185                           190

Asn  Arg  Gln  Ile  Arg  Glu  Ile  His  Glu  Tyr  Ser  Asn  His  Cys  Val  Asp
          195                      200                 205

Thr  Tyr  Asn  Thr  Glu  Leu  Glu  Arg  Leu  Gly  Phe  Arg  Ser  Ile  Ala  Gln
     210                      215                      220

Trp  Arg  Ile  Tyr  Asn  Gln  Phe  Arg  Arg  Glu  Leu  Thr  Leu  Thr  Val  Leu
225                      230                      235                      240

Asp  Ile  Val  Ala  Leu  Phe  Pro  Asn  Tyr  Asp  Ser  Arg  Leu  Tyr  Pro  Ile
               245                      250                      255

Gln  Thr  Phe  Ser  Gln  Leu  Thr  Arg  Glu  Ile  Val  Thr  Ser  Pro  Val  Ser
               260                      265                      270

Glu  Phe  Tyr  Tyr  Gly  Val  Ile  Asn  Ser  Gly  Asn  Ile  Ile  Gly  Thr  Leu
          275                      280                      285

Thr  Glu  Gln  Gln  Ile  Arg  Arg  Pro  His  Leu  Met  Asp  Phe  Phe  Asn  Ser
     290                      295                      300

Met  Ile  Met  Tyr  Thr  Ser  Asp  Asn  Arg  Arg  Glu  His  Tyr  Trp  Ser  Gly
305                      310                      315                      320

Leu  Glu  Met  Thr  Ala  Tyr  Phe  Thr  Gly  Phe  Ala  Gly  Ala  Gln  Val  Ser
                    325                      330                      335

Phe  Pro  Leu  Val  Gly  Thr  Arg  Gly  Glu  Ser  Ala  Pro  Pro  Leu  Thr  Val
               340                      345                      350

Arg  Ser  Val  Asn  Asp  Gly  Ile  Tyr  Arg  Ile  Leu  Ser  Ala  Pro  Phe  Tyr
          355                      360                      365

Ser  Ala  Pro  Phe  Leu  Gly  Thr  Ile  Val  Leu  Gly  Ser  Arg  Gly  Glu  Lys
     370                      375                      380

Phe  Asp  Phe  Ala  Leu  Asn  Asn  Ile  Ser  Pro  Pro  Ser  Thr  Ile  Tyr
385                      390                      395                      400

Arg  His  Pro  Gly  Thr  Val  Asp  Ser  Leu  Val  Ser  Ile  Pro  Pro  Gln  Asp
                    405                      410                      415

Asn  Ser  Val  Pro  Pro  His  Arg  Gly  Ser  Ser  His  Arg  Leu  Ser  His  Val
               420                      425                      430

Thr  Met  Arg  Ala  Ser  Ser  Pro  Ile  Phe  His  Trp  Thr  His  Arg  Ser  Ala
          435                      440                      445

Thr  Thr  Thr  Asn  Thr  Ile  Asn  Pro  Asn  Ala  Ile  Ile  Gln  Ile  Pro  Leu
     450                      455                      460

Val  Lys  Ala  Phe  Asn  Leu  His  Ser  Gly  Ala  Thr  Val  Val  Arg  Gly  Pro
465                      470                      475                      480

Gly  Phe  Thr  Gly  Gly  Asp  Ile  Leu  Arg  Arg  Thr  Asn  Thr  Gly  Thr  Phe
                    485                      490                      495

Ala  Asp  Met  Arg  Val  Asn  Ile  Thr  Gly  Pro  Leu  Ser  Gln  Arg  Tyr  Arg
               500                      505                      510

Val  Arg  Ile  Arg  Tyr  Ala  Ser  Thr  Thr  Asp  Leu  Gln  Phe  Phe  Thr  Arg
          515                      520                      525

Ile  Asn  Gly  Thr  Ser  Val  Asn  Gln  Gly  Asn  Phe  Gln  Arg  Thr  Met  Asn
     530                      535                      540

Arg  Gly  Asp  Asn  Leu  Glu  Ser  Gly  Asn  Phe  Arg  Thr  Ala  Gly  Phe  Ser
545                      550                      555                      560
```

| | | | | | | | | | | | | | | |
|---|---|---|---|---|---|---|---|---|---|---|---|---|---|---|
|Thr|Pro|Phe|Ser|Phe|Ser|Asn|Ala|Gln|Ser|Thr|Phe|Thr|Leu|Gly|Thr|
| | | | |565| | | |570| | | |575| | |
|Gln|Ala|Phe|Ser|Asn|Gln|Glu|Val|Tyr|Ile|Asp|Arg|Ile|Glu|Phe|Val|
| | | |580| | | |585| | | |590| | | |
|Pro|Ala|Glu|Val|Thr|Phe|Glu|Ala|Glu|Ser|Asp|Leu|Glu|Arg|Ala|Gln|
| | |595| | | |600| | | |605| | | | |
|Lys|Ala|Val|Asn|Ala|Leu|Phe|Thr|Ser|Thr|Asn|Gln|Leu|Gly|Leu|Lys|
| |610| | | | |615| | | |620| | | | |
|Thr|Asp|Val|Thr|Asp|Tyr|Gln|Ile|Asp|Gln|Val|Ser|Asn|Leu|Val|Glu|
|625| | | |630| | | |635| | | | | |640|
|Cys|Leu|Ser|Asp|Glu|Phe|Cys|Leu|Asp|Glu|Lys|Arg|Glu|Leu|Ser|Glu|
| | | |645| | | |650| | | |655| | | |
|Lys|Val|Lys|His|Ala|Lys|Arg|Leu|Ser|Asp|Lys|Arg|Asn|Leu|Leu|Gln|
| | |660| | | |665| | | |670| | | | |
|Asp|Pro|Asn|Phe|Thr|Ser|Ile|Asn|Arg|Gln|Leu|Asp|Arg|Gly|Trp|Arg|
| |675| | | |680| | | |685| | | | | |
|Gly|Ser|Thr|Asp|Ile|Thr|Ile|Gln|Gly|Gly|Asn|Asp|Val|Phe|Lys|Glu|
|690| | | |695| | | |700| | | | | | |
|Asn|Tyr|Val|Thr|Leu|Pro|Gly|Thr|Phe|Asp|Glu|Cys|Tyr|Pro|Thr|Tyr|
|705| | | |710| | | |715| | | | | |720|
|Leu|Tyr|Gln|Lys|Ile|Asp|Glu|Ser|Lys|Leu|Lys|Ala|Tyr|Thr|Arg|Tyr|
| | | |725| | | |730| | | |735| | | |
|Glu|Leu|Arg|Gly|Tyr|Ile|Glu|Asp|Ser|Gln|Asp|Leu|Glu|Val|Tyr|Leu|
| | |740| | | |745| | | |750| | | | |
|Ile|Arg|Tyr|Asn|Ala|Lys|His|Glu|Thr|Val|Asn|Val|Pro|Gly|Thr|Gly|
| |755| | | |760| | | |765| | | | | |
|Ser|Leu|Trp|Pro|Leu|Ser|Val|Glu|Ser|Pro|Ile|Gly|Arg|Cys|Gly|Glu|
|770| | | |775| | | |780| | | | | | |
|Pro|Asn|Arg|Cys|Val|Pro|His|Ile|Glu|Trp|Asn|Pro|Asp|Leu|Asp|Cys|
|785| | | |790| | | |795| | | | | |800|
|Ser|Cys|Arg|Asp|Gly|Glu|Lys|Cys|Ala|His|His|Ser|His|His|Phe|Ser|
| | | |805| | | |810| | | |815| | | |
|Leu|Asp|Ile|Asp|Val|Gly|Cys|Thr|Asp|Leu|Asn|Glu|Asp|Leu|Gly|Val|
| | |820| | | |825| | | |830| | | | |
|Trp|Val|Ile|Phe|Lys|Ile|Lys|Thr|Gln|Asp|Gly|His|Ala|Arg|Leu|Gly|
| |835| | | |840| | | |845| | | | | |
|Asn|Leu|Glu|Phe|Leu|Glu|Glu|Lys|Pro|Leu|Leu|Gly|Glu|Ala|Leu|Ala|
|850| | | |855| | | |860| | | | | | |
|Arg|Val|Lys|Arg|Ala|Glu|Lys|Lys|Trp|Arg|Asp|Lys|Arg|Glu|Gln|Leu|
|865| | | |870| | | |875| | | | | |880|
|Gln|Phe|Glu|Thr|Asn|Ile|Val|Tyr|Lys|Glu|Ala|Lys|Glu|Ser|Val|Asp|
| | | |885| | | |890| | | |895| | | |
|Ala|Leu|Phe|Val|Asp|Ser|His|Tyr|Asn|Arg|Leu|Gln|Ala|Asp|Thr|Asn|
| | |900| | | |905| | | |910| | | | |
|Ile|Thr|Met|Ile|His|Ala|Ala|Asp|Lys|Arg|Val|His|Arg|Ile|Arg|Glu|
| |915| | | |920| | | |925| | | | | |
|Ala|Tyr|Leu|Pro|Glu|Leu|Ser|Val|Ile|Pro|Gly|Val|Asn|Ala|Asp|Ile|
|930| | | |935| | | |940| | | | | | |
|Phe|Glu|Glu|Leu|Glu|Gly|Leu|Ile|Phe|Thr|Ala|Phe|Ser|Leu|Tyr|Asp|
|945| | | |950| | | |955| | | | | |960|
|Ala|Arg|Asn|Ile|Ile|Lys|Asn|Gly|Asp|Phe|Asn|Asn|Gly|Leu|Ser|Cys|
| | | |965| | | |970| | | |975| | | |
|Trp|Asn|Val|Lys|Gly|His|Val|Asp|Ile|Gln|Gln|Asn|Asp|His|Arg|Ser|

-continued

```
                        980                           985                             990
Val   Leu   Val   Val   Pro   Glu   Trp   Glu   Ser   Glu   Val   Ser   Gln   Glu   Val   Arg
                  995                           1000                          1005

Val   Cys   Pro   Gly   Arg   Gly   Tyr   Ile   Leu   Arg   Val   Thr   Ala   Tyr   Lys   Glu
      1010                          1015                          1020

Gly   Tyr   Gly   Glu   Gly   Cys   Val   Thr   Ile   His   Glu   Ile   Glu   Asp   Asn   Thr
1025                          1030                          1035                          1040

Asp   Glu   Leu   Lys   Phe   Ser   Asn   Cys   Ile   Glu   Glu   Val   Tyr   Pro   Thr
                        1045                          1050                          1055

Asp   Thr   Gly   Asn   Asp   Tyr   Thr   Ala   His   Gln   Gly   Thr   Thr   Gly   Cys   Ala
                  1060                          1065                          1070

Asp   Ala   Cys   Asn   Ser   Arg   Asn   Val   Gly   Tyr   Glu   Asp   Gly   Tyr   Glu   Ile
      1075                          1080                          1085

Asn   Thr   Thr   Ala   Ser   Val   Asn   Tyr   Lys   Pro   Thr   Tyr   Glu   Glu   Glu   Met
      1090                          1095                          1100

Tyr   Thr   Asp   Val   Arg   Arg   Asp   Asn   His   Cys   Glu   Tyr   Asp   Arg   Gly   Tyr
1105                          1110                          1115                          1120

Gly   Asn   His   Thr   Pro   Leu   Pro   Ala   Gly   Tyr   Val   Thr   Lys   Glu   Leu   Glu
                        1125                          1130                          1135

Tyr   Phe   Pro   Glu   Thr   Asp   Thr   Val   Trp   Ile   Glu   Ile   Gly   Glu   Thr   Glu
                  1140                          1145                          1150

Gly   Thr   Phe   Ile   Val   Asp   Ser   Val   Glu   Leu   Leu   Leu   Met   Glu   Glu
            1155                          1160                          1165
```

( 2 ) INFORMATION FOR SEQ ID NO:3:

( i ) SEQUENCE CHARACTERISTICS:
        ( A ) LENGTH: 3934 base pairs
        ( B ) TYPE: nucleic acid
        ( C ) STRANDEDNESS: double
        ( D ) TOPOLOGY: circular ( i i ) MOLECULE TYPE: DNA (genomic)

( i x ) FEATURE:
        ( A ) NAME/KEY: CDS
        ( B ) LOCATION: 67..3756

( i x ) FEATURE:
        ( A ) NAME/KEY: misc_feature
        ( B ) LOCATION: 2253..2272

( x i ) SEQUENCE DESCRIPTION: SEQ ID NO:3:

```
AAACTATTCA   ATGGAGAAAA   ATTGAATAGT   TGTAATGTAA   GCACACCGAA   AAAAGGAGGA                    60

GTTATA   TTG   ACT   TCA   AAT   AGG   AAA   AAT   GAG   AAT   GAA   ATT   ATA   AAT   GCT     108
         Leu   Thr   Ser   Asn   Arg   Lys   Asn   Glu   Asn   Glu   Ile   Ile   Asn   Ala
         1                 5                             10

TTA   TCG   ATT   CCA   ACG   GTA   TCG   AAT   CCT   TCC   ACG   CAA   ATG   AAT   CTA   TCA   156
Leu   Ser   Ile   Pro   Thr   Val   Ser   Asn   Pro   Ser   Thr   Gln   Met   Asn   Leu   Ser
15                      20                              25                            30

CCA   GAT   GCT   CGT   ATT   GAA   GAT   AGC   TTG   TGT   GTA   GCC   GAG   GTG   AAC   AAT   204
Pro   Asp   Ala   Arg   Ile   Glu   Asp   Ser   Leu   Cys   Val   Ala   Glu   Val   Asn   Asn
                        35                              40                            45

ATT   GAT   CCA   TTT   GTT   AGC   GCA   TCA   ACA   GTC   CAA   ACG   GGT   ATA   AAC   ATA   252
Ile   Asp   Pro   Phe   Val   Ser   Ala   Ser   Thr   Val   Gln   Thr   Gly   Ile   Asn   Ile
                  50                              55                            60

GCT   GGT   AGA   ATA   TTG   GGC   GTA   TTA   GGT   GTG   CCG   TTT   GCT   GGA   CAA   CTA   300
Ala   Gly   Arg   Ile   Leu   Gly   Val   Leu   Gly   Val   Pro   Phe   Ala   Gly   Gln   Leu
            65                              70                            75

GCT   AGT   TTT   TAT   AGT   TTT   CTT   GTT   GGG   GAA   TTA   TGG   CCT   AGT   GGC   AGA   348
Ala   Ser   Phe   Tyr   Ser   Phe   Leu   Val   Gly   Glu   Leu   Trp   Pro   Ser   Gly   Arg
```

```
                80                           85                           90
GAT  CCA  TGG  GAA  ATT  TTC  CTG  GAA  CAT  GTA  GAA  CAA  CTT  ATA  AGA  CAA      396
Asp  Pro  Trp  Glu  Ile  Phe  Leu  Glu  His  Val  Glu  Gln  Leu  Ile  Arg  Gln
 95            100                      105                           110

CAA  GTA  ACA  GAA  AAT  ACT  AGG  AAT  ACG  GCT  ATT  GCT  CGA  TTA  GAA  GGT      444
Gln  Val  Thr  Glu  Asn  Thr  Arg  Asn  Thr  Ala  Ile  Ala  Arg  Leu  Glu  Gly
                    115                      120                      125

CTA  GGA  AGA  GGC  TAT  AGA  TCT  TAC  CAG  CAG  GCT  CTT  GAA  ACT  TGG  TTA      492
Leu  Gly  Arg  Gly  Tyr  Arg  Ser  Tyr  Gln  Gln  Ala  Leu  Glu  Thr  Trp  Leu
               130                      135                      140

GAT  AAC  CGA  AAT  GAT  GCA  AGA  TCA  AGA  AGC  ATT  ATT  CTT  GAG  CGC  TAT      540
Asp  Asn  Arg  Asn  Asp  Ala  Arg  Ser  Arg  Ser  Ile  Ile  Leu  Glu  Arg  Tyr
               145                      150                      155

GTT  GCT  TTA  GAA  CTT  GAC  ATT  ACT  ACT  GCT  ATA  CCG  CTT  TTC  AGA  ATA      588
Val  Ala  Leu  Glu  Leu  Asp  Ile  Thr  Thr  Ala  Ile  Pro  Leu  Phe  Arg  Ile
     160                      165                      170

CGA  AAT  GAA  GAA  GTT  CCA  TTA  TTA  ATG  GTA  TAT  GCT  CAA  GCT  GCA  AAT      636
Arg  Asn  Glu  Glu  Val  Pro  Leu  Leu  Met  Val  Tyr  Ala  Gln  Ala  Ala  Asn
175                      180                      185                      190

TTA  CAC  CTA  TTA  TTA  TTG  AGA  GAC  GCA  TCC  CTT  TTT  GGT  AGT  GAA  TGG      684
Leu  His  Leu  Leu  Leu  Leu  Arg  Asp  Ala  Ser  Leu  Phe  Gly  Ser  Glu  Trp
                    195                      200                      205

GGG  ATG  GCA  TCT  TCC  GAT  GTT  AAC  CAA  TAT  TAC  CAA  GAA  CAA  ATC  AGA      732
Gly  Met  Ala  Ser  Ser  Asp  Val  Asn  Gln  Tyr  Tyr  Gln  Glu  Gln  Ile  Arg
               210                      215                      220

TAT  ACA  GAG  GAA  TAT  TCT  AAC  CAT  TGC  GTA  CAA  TGG  TAT  AAT  ACA  GGG      780
Tyr  Thr  Glu  Glu  Tyr  Ser  Asn  His  Cys  Val  Gln  Trp  Tyr  Asn  Thr  Gly
          225                      230                      235

CTA  AAT  AAC  TTA  AGA  GGG  ACA  AAT  GCT  GAA  AGT  TGG  TTG  CGG  TAT  AAT      828
Leu  Asn  Asn  Leu  Arg  Gly  Thr  Asn  Ala  Glu  Ser  Trp  Leu  Arg  Tyr  Asn
240                      245                      250

CAA  TTC  CGT  AGA  GAC  CTA  ACG  TTA  GGG  GTA  TTA  GAT  TTA  GTA  GCC  CTA      876
Gln  Phe  Arg  Arg  Asp  Leu  Thr  Leu  Gly  Val  Leu  Asp  Leu  Val  Ala  Leu
255                      260                      265                      270

TTC  CCA  AGC  TAT  GAT  ACT  CGC  ACT  TAT  CCA  ATC  AAT  ACG  AGT  GCT  CAG      924
Phe  Pro  Ser  Tyr  Asp  Thr  Arg  Thr  Tyr  Pro  Ile  Asn  Thr  Ser  Ala  Gln
                    275                      280                      285

TTA  ACA  AGA  GAA  ATT  TAT  ACA  GAT  CCA  ATT  GGG  AGA  ACA  AAT  GCA  CCT      972
Leu  Thr  Arg  Glu  Ile  Tyr  Thr  Asp  Pro  Ile  Gly  Arg  Thr  Asn  Ala  Pro
               290                      295                      300

TCA  GGA  TTT  GCA  AGT  ACG  AAT  TGG  TTT  AAT  AAT  AAT  GCA  CCA  TCG  TTT     1020
Ser  Gly  Phe  Ala  Ser  Thr  Asn  Trp  Phe  Asn  Asn  Asn  Ala  Pro  Ser  Phe
          305                      310                      315

TCT  GCC  ATA  GAG  GCT  GCC  ATT  TTC  AGG  CCT  CCG  CAT  CTA  CTT  GAT  TTT     1068
Ser  Ala  Ile  Glu  Ala  Ala  Ile  Phe  Arg  Pro  Pro  His  Leu  Leu  Asp  Phe
320                      325                      330

CCA  GAA  CAA  CTT  ACA  ATT  TAC  AGT  GCA  TCA  AGC  CGT  TGG  AGT  AGC  ACT     1116
Pro  Glu  Gln  Leu  Thr  Ile  Tyr  Ser  Ala  Ser  Ser  Arg  Trp  Ser  Ser  Thr
335                      340                      345                      350

CAA  CAT  ATG  AAT  TAT  TGG  GTG  GGA  CAT  AGG  CTT  AAC  TTC  CGC  CCA  ATA     1164
Gln  His  Met  Asn  Tyr  Trp  Val  Gly  His  Arg  Leu  Asn  Phe  Arg  Pro  Ile
                    355                      360                      365

GGA  GGG  ACA  TTA  AAT  ACC  TCA  ACA  CAA  GGA  CTT  ACT  AAT  AAT  ACT  TCA     1212
Gly  Gly  Thr  Leu  Asn  Thr  Ser  Thr  Gln  Gly  Leu  Thr  Asn  Asn  Thr  Ser
               370                      375                      380

ATT  AAT  CCT  GTA  ACA  TTA  CAG  TTT  ACG  TCT  CGA  GAC  GTT  TAT  AGA  ACA     1260
Ile  Asn  Pro  Val  Thr  Leu  Gln  Phe  Thr  Ser  Arg  Asp  Val  Tyr  Arg  Thr
          385                      390                      395

GAA  TCA  AAT  GCA  GGG  ACA  AAT  ATA  CTA  TTT  ACT  ACT  CCT  GTG  AAT  GGA     1308
Glu  Ser  Asn  Ala  Gly  Thr  Asn  Ile  Leu  Phe  Thr  Thr  Pro  Val  Asn  Gly
```

-continued

```
              400                            405                            410
GTA  CCT  TGG  GCT  AGA  TTT  AAT  TTT  ATA  AAC  CCT  CAG  AAT  ATT  TAT  GAA      1356
Val  Pro  Trp  Ala  Arg  Phe  Asn  Phe  Ile  Asn  Pro  Gln  Asn  Ile  Tyr  Glu
415                 420                      425                           430

AGA  GGC  GCC  ACT  ACC  TAC  AGT  CAA  CCG  TAT  CAG  GGA  GTT  GGG  ATT  CAA      1404
Arg  Gly  Ala  Thr  Thr  Tyr  Ser  Gln  Pro  Tyr  Gln  Gly  Val  Gly  Ile  Gln
                    435                      440                      445

TTA  TTT  GAT  TCA  GAA  ACT  GAA  TTA  CCA  GAA  ACA  ACA  GAA  CGA  CCA          1452
Leu  Phe  Asp  Ser  Glu  Thr  Glu  Leu  Pro  Glu  Thr  Thr  Glu  Arg  Pro
               450                      455                      460

AAT  TAT  GAA  TCA  TAT  AGT  CAT  AGA  TTA  TCT  CAT  ATA  GGA  CTA  ATC  ATA      1500
Asn  Tyr  Glu  Ser  Tyr  Ser  His  Arg  Leu  Ser  His  Ile  Gly  Leu  Ile  Ile
               465                 470                      475

GGA  AAC  ACT  TTG  AGA  GCA  CCA  GTC  TAT  TCT  TGG  ACG  CAT  CGT  AGT  GCA      1548
Gly  Asn  Thr  Leu  Arg  Ala  Pro  Val  Tyr  Ser  Trp  Thr  His  Arg  Ser  Ala
          480                      485                      490

GAT  CGT  ACG  AAT  ACG  ATT  GGA  CCA  AAT  AGA  ATT  ACA  CAA  ATA  CCA  TTG      1596
Asp  Arg  Thr  Asn  Thr  Ile  Gly  Pro  Asn  Arg  Ile  Thr  Gln  Ile  Pro  Leu
495                      500                      505                      510

GTA  AAA  GCA  CTG  AAT  CTT  CAT  TCA  GGT  GTT  ACT  GTT  GTT  GGA  GGG  CCA      1644
Val  Lys  Ala  Leu  Asn  Leu  His  Ser  Gly  Val  Thr  Val  Val  Gly  Gly  Pro
                         515                      520                      525

GGA  TTT  ACA  GGT  GGG  GAT  ATC  CTT  CGT  AGA  ACA  AAT  ACG  GGT  ACA  TTT      1692
Gly  Phe  Thr  Gly  Gly  Asp  Ile  Leu  Arg  Arg  Thr  Asn  Thr  Gly  Thr  Phe
               530                      535                      540

GGA  GAT  ATA  CGA  TTA  AAT  ATT  AAT  GTG  CCA  TTA  TCC  CAA  AGA  TAT  CGC      1740
Gly  Asp  Ile  Arg  Leu  Asn  Ile  Asn  Val  Pro  Leu  Ser  Gln  Arg  Tyr  Arg
               545                      550                      555

GTA  AGG  ATT  CGT  TAT  GCT  TCT  ACT  ACA  GAT  TTA  CAA  TTT  TTC  ACG  AGA      1788
Val  Arg  Ile  Arg  Tyr  Ala  Ser  Thr  Thr  Asp  Leu  Gln  Phe  Phe  Thr  Arg
               560                 565                      570

ATT  AAT  GGA  ACC  ACT  GTT  AAT  ATT  GGT  AAT  TTC  TCA  AGA  ACT  ATG  AAT      1836
Ile  Asn  Gly  Thr  Thr  Val  Asn  Ile  Gly  Asn  Phe  Ser  Arg  Thr  Met  Asn
575                      580                      585                      590

AGG  GGG  GAT  AAT  TTA  GAA  TAT  AGA  AGT  TTT  AGA  ACT  GCA  GGA  TTT  AGT      1884
Arg  Gly  Asp  Asn  Leu  Glu  Tyr  Arg  Ser  Phe  Arg  Thr  Ala  Gly  Phe  Ser
               595                      600                      605

ACT  CCT  TTT  AAT  TTT  TTA  AAT  GCC  CAA  AGC  ACA  TTC  ACA  TTG  GGT  GCT      1932
Thr  Pro  Phe  Asn  Phe  Leu  Asn  Ala  Gln  Ser  Thr  Phe  Thr  Leu  Gly  Ala
               610                      615                      620

CAG  AGT  TTT  TCA  AAT  CAG  GAA  GTT  TAT  ATA  GAT  AGA  GTC  GAA  TTT  GTT      1980
Gln  Ser  Phe  Ser  Asn  Gln  Glu  Val  Tyr  Ile  Asp  Arg  Val  Glu  Phe  Val
          625                      630                      635

CCA  GCA  GAG  GTA  ACA  TTT  GAG  GCA  GAA  TAT  GAT  TTA  GAA  AGA  GCA  CAA      2028
Pro  Ala  Glu  Val  Thr  Phe  Glu  Ala  Glu  Tyr  Asp  Leu  Glu  Arg  Ala  Gln
          640                      645                      650

AAG  GCG  GTG  AAT  GCT  CTG  TTT  ACT  TCT  ACA  AAT  CCA  AGA  AGA  TTG  AAA      2076
Lys  Ala  Val  Asn  Ala  Leu  Phe  Thr  Ser  Thr  Asn  Pro  Arg  Arg  Leu  Lys
655                      660                      665                      670

ACA  GAT  GTG  ACA  GAT  TAT  CAT  ATT  GAC  CAA  GTG  TCC  AAT  ATG  GTG  GCA      2124
Thr  Asp  Val  Thr  Asp  Tyr  His  Ile  Asp  Gln  Val  Ser  Asn  Met  Val  Ala
                    675                      680                      685

TGT  TTA  TCA  GAT  GAA  TTT  TGC  TTG  GAT  GAG  AAG  CGA  GAA  TTA  TTT  GAG      2172
Cys  Leu  Ser  Asp  Glu  Phe  Cys  Leu  Asp  Glu  Lys  Arg  Glu  Leu  Phe  Glu
               690                      695                      700

AAA  GTG  AAA  TAT  GCG  AAG  CGA  CTC  AGT  GAT  GAA  AGA  AAC  TTA  CTC  CAA      2220
Lys  Val  Lys  Tyr  Ala  Lys  Arg  Leu  Ser  Asp  Glu  Arg  Asn  Leu  Leu  Gln
               705                      710                      715

GAT  CCA  AAC  TTC  ACA  TTC  ATC  AGT  GGG  CAA  TTA  AGT  TTC  GCA  TCC  ATC      2268
Asp  Pro  Asn  Phe  Thr  Phe  Ile  Ser  Gly  Gln  Leu  Ser  Phe  Ala  Ser  Ile
```

-continued

|  |  |  | 720 |  |  |  |  | 725 |  |  |  |  | 730 |  |  |  |
|---|---|---|---|---|---|---|---|---|---|---|---|---|---|---|---|---|
| GAT | GGA | CAA | TCA | AAC | TTC | CCC | TCT | ATT | AAT | GAG | CTA | TCT | GAA | CAT | GGA | 2316 |
| Asp | Gly | Gln | Ser | Asn | Phe | Pro | Ser | Ile | Asn | Glu | Leu | Ser | Glu | His | Gly |  |
| 735 |  |  |  | 740 |  |  |  |  | 745 |  |  |  |  |  | 750 |  |
| TGG | TGG | GGA | AGT | GCG | AAT | GTT | ACC | ATT | CAG | GAA | GGG | AAT | GAC | GTA | TTT | 2364 |
| Trp | Trp | Gly | Ser | Ala | Asn | Val | Thr | Ile | Gln | Glu | Gly | Asn | Asp | Val | Phe |  |
|  |  |  |  | 755 |  |  |  |  | 760 |  |  |  |  | 765 |  |  |
| AAA | GAG | AAT | TAC | GTC | ACA | CTA | CCG | GGT | ACT | TTT | AAT | GAG | TGT | TAT | CCA | 2412 |
| Lys | Glu | Asn | Tyr | Val | Thr | Leu | Pro | Gly | Thr | Phe | Asn | Glu | Cys | Tyr | Pro |  |
|  |  |  | 770 |  |  |  |  | 775 |  |  |  |  |  | 780 |  |  |
| AAT | TAT | TTA | TAT | CAA | AAA | ATA | GGA | GAG | TCA | GAA | TTA | AAA | GCT | TAT | ACG | 2460 |
| Asn | Tyr | Leu | Tyr | Gln | Lys | Ile | Gly | Glu | Ser | Glu | Leu | Lys | Ala | Tyr | Thr |  |
|  |  | 785 |  |  |  |  | 790 |  |  |  |  | 795 |  |  |  |  |
| CGC | TAT | CAA | TTA | AGA | GGG | TAT | ATT | GAA | GAT | AGT | CAA | GAT | CTA | GAG | ATT | 2508 |
| Arg | Tyr | Gln | Leu | Arg | Gly | Tyr | Ile | Glu | Asp | Ser | Gln | Asp | Leu | Glu | Ile |  |
|  | 800 |  |  |  |  | 805 |  |  |  |  | 810 |  |  |  |  |  |
| TAT | TTA | ATT | CGT | TAC | AAT | GCA | AAG | CAT | GAA | ACA | TTG | GAT | GTT | CCA | GGT | 2556 |
| Tyr | Leu | Ile | Arg | Tyr | Asn | Ala | Lys | His | Glu | Thr | Leu | Asp | Val | Pro | Gly |  |
| 815 |  |  |  |  | 820 |  |  |  |  | 825 |  |  |  |  | 830 |  |
| ACC | GAT | TCC | CTA | TGG | CCG | CTT | TCA | GTT | GAA | AGC | CCA | ATC | GGA | AGG | TGC | 2604 |
| Thr | Asp | Ser | Leu | Trp | Pro | Leu | Ser | Val | Glu | Ser | Pro | Ile | Gly | Arg | Cys |  |
|  |  |  |  | 835 |  |  |  |  | 840 |  |  |  |  | 845 |  |  |
| GGA | GAA | CCA | AAT | CGA | TGC | GCA | CCA | CAT | TTT | GAA | TGG | AAT | CCT | GAT | CTA | 2652 |
| Gly | Glu | Pro | Asn | Arg | Cys | Ala | Pro | His | Phe | Glu | Trp | Asn | Pro | Asp | Leu |  |
|  |  |  | 850 |  |  |  |  | 855 |  |  |  |  | 860 |  |  |  |
| GAT | TGT | TCC | TGC | AGA | GAT | GGA | GAA | AGA | TGT | GCG | CAT | CAT | TCC | CAT | CAT | 2700 |
| Asp | Cys | Ser | Cys | Arg | Asp | Gly | Glu | Arg | Cys | Ala | His | His | Ser | His | His |  |
|  |  | 865 |  |  |  |  | 870 |  |  |  |  | 875 |  |  |  |  |
| TTC | ACT | TTG | GAT | ATT | GAT | GTT | GGG | TGC | ACA | GAC | TTG | CAT | GAG | AAC | CTA | 2748 |
| Phe | Thr | Leu | Asp | Ile | Asp | Val | Gly | Cys | Thr | Asp | Leu | His | Glu | Asn | Leu |  |
| 880 |  |  |  |  | 885 |  |  |  |  | 890 |  |  |  |  |  |  |
| GGC | GTG | TGG | GTG | GTA | TTC | AAG | ATT | AAG | ACG | CAG | GAA | GGT | TAT | GCA | AGA | 2796 |
| Gly | Val | Trp | Val | Val | Phe | Lys | Ile | Lys | Thr | Gln | Glu | Gly | Tyr | Ala | Arg |  |
| 895 |  |  |  |  | 900 |  |  |  |  | 905 |  |  |  |  | 910 |  |
| TTA | GGA | AAT | CTG | GAA | TTT | ATC | GAA | GAG | AAA | CCA | TTA | ATT | GGA | GAA | GCA | 2844 |
| Leu | Gly | Asn | Leu | Glu | Phe | Ile | Glu | Glu | Lys | Pro | Leu | Ile | Gly | Glu | Ala |  |
|  |  |  |  | 915 |  |  |  |  | 920 |  |  |  |  | 925 |  |  |
| CTG | TCT | CGT | GTG | AAG | AGA | GCG | GAA | AAA | AAA | TGG | AGA | GAC | AAA | CGG | GAA | 2892 |
| Leu | Ser | Arg | Val | Lys | Arg | Ala | Glu | Lys | Lys | Trp | Arg | Asp | Lys | Arg | Glu |  |
|  |  |  | 930 |  |  |  |  | 935 |  |  |  |  | 940 |  |  |  |
| AAA | CTA | CAA | TTG | GAA | ACA | AAA | CGA | GTA | TAT | ACA | GAG | GCA | AAA | GAA | GCT | 2940 |
| Lys | Leu | Gln | Leu | Glu | Thr | Lys | Arg | Val | Tyr | Thr | Glu | Ala | Lys | Glu | Ala |  |
|  |  | 945 |  |  |  |  | 950 |  |  |  |  | 955 |  |  |  |  |
| GTG | GAT | GCT | TTA | TTC | GTA | GAT | TCT | CAA | TAT | GAT | CAA | TTA | CAA | GCG | GAT | 2988 |
| Val | Asp | Ala | Leu | Phe | Val | Asp | Ser | Gln | Tyr | Asp | Gln | Leu | Gln | Ala | Asp |  |
|  | 960 |  |  |  |  | 965 |  |  |  |  | 970 |  |  |  |  |  |
| ACA | AAC | ATT | GGC | ATG | ATT | CAT | GCG | GCA | GAT | AAA | CTT | GTT | CAT | CGA | ATT | 3036 |
| Thr | Asn | Ile | Gly | Met | Ile | His | Ala | Ala | Asp | Lys | Leu | Val | His | Arg | Ile |  |
| 975 |  |  |  |  | 980 |  |  |  |  | 985 |  |  |  |  | 990 |  |
| CGA | GAG | GCG | TAT | CTT | TCA | GAA | TTA | CCT | GTT | ATC | CCA | GGT | GTA | AAT | GCG | 3084 |
| Arg | Glu | Ala | Tyr | Leu | Ser | Glu | Leu | Pro | Val | Ile | Pro | Gly | Val | Asn | Ala |  |
|  |  |  |  | 995 |  |  |  |  | 1000 |  |  |  |  | 1005 |  |  |
| GAA | ATT | TTT | GAA | GAA | TTA | GAA | GGT | CAC | ATT | ATC | ACT | GCA | ATG | TCC | TTA | 3132 |
| Glu | Ile | Phe | Glu | Glu | Leu | Glu | Gly | His | Ile | Ile | Thr | Ala | Met | Ser | Leu |  |
|  |  |  |  | 1010 |  |  |  |  | 1015 |  |  |  |  | 1020 |  |  |
| TAC | GAT | GCG | AGA | AAT | GTC | GTT | AAA | AAT | GGT | GAT | TTT | AAT | AAT | GGA | TTA | 3180 |
| Tyr | Asp | Ala | Arg | Asn | Val | Val | Lys | Asn | Gly | Asp | Phe | Asn | Asn | Gly | Leu |  |
|  |  |  | 1025 |  |  |  |  | 1030 |  |  |  |  | 1035 |  |  |  |
| ACA | TGT | TGG | AAT | GTA | AAA | GGG | CAT | GTA | GAT | GTA | CAA | CAG | AGC | CAT | CAT | 3228 |
| Thr | Cys | Trp | Asn | Val | Lys | Gly | His | Val | Asp | Val | Gln | Gln | Ser | His | His |  |

|  |  |  |  |  |  |  |  |  |  |  |  |  |  |  |  |
|---|---|---|---|---|---|---|---|---|---|---|---|---|---|---|---|
| | | | | 1040 | | | | | 1045 | | | | | 1050 | |

```
CGT TCT GAC CTT GTT ATC CCA GAA TGG GAA GCA GAA GTG TCA CAA GCA     3276
Arg Ser Asp Leu Val Ile Pro Glu Trp Glu Ala Glu Val Ser Gln Ala
1055            1060                1065                1070

GTT CGC GTC TGT CCG GGG CGT GGC TAT ATC CTT CGT GTC ACA GCG TAC     3324
Val Arg Val Cys Pro Gly Arg Gly Tyr Ile Leu Arg Val Thr Ala Tyr
                1075                1080                1085

AAA GAG GGA TAT GGA GAG GGC TGC GTA ACG ATC CAT GAA ATC GAG AAC     3372
Lys Glu Gly Tyr Gly Glu Gly Cys Val Thr Ile His Glu Ile Glu Asn
            1090                1095                1100

AAT ACA GAC GAA CTA AAA TTT AAA AAC TGT GAA GAA GAG GAA GTG TAT     3420
Asn Thr Asp Glu Leu Lys Phe Lys Asn Cys Glu Glu Glu Glu Val Tyr
        1105                1110                1115

CCA ACG GAT ACA GGA ACG TGT AAT GAT TAT ACT GCA CAC CAA GGT ACA     3468
Pro Thr Asp Thr Gly Thr Cys Asn Asp Tyr Thr Ala His Gln Gly Thr
    1120                1125                1130

GCA GCA TGT AAT TCC CGT AAT GCT GGA TAT GAG GAT GCA TAT GAA GTT     3516
Ala Ala Cys Asn Ser Arg Asn Ala Gly Tyr Glu Asp Ala Tyr Glu Val
1135                1140                1145                1150

GAT ACT ACA GCA TCT GTT AAT TAC AAA CCG ACT TAT GAA GAA GAA ACG     3564
Asp Thr Thr Ala Ser Val Asn Tyr Lys Pro Thr Tyr Glu Glu Glu Thr
                1155                1160                1165

TAT ACA GAT GTA CGA AGA GAT AAT CAT TGT GAA TAT GAC AGA GGG TAT     3612
Tyr Thr Asp Val Arg Arg Asp Asn His Cys Glu Tyr Asp Arg Gly Tyr
            1170                1175                1180

GTG AAT TAT CCA CCA GTA CCA GCT GGT TAT GTG ACA AAA GAA TTA GAA     3660
Val Asn Tyr Pro Pro Val Pro Ala Gly Tyr Val Thr Lys Glu Leu Glu
        1185                1190                1195

TAC TTC CCA GAA ACA GAT ACA GTA TGG ATT GAG ATT GGA GAA ACG GAA     3708
Tyr Phe Pro Glu Thr Asp Thr Val Trp Ile Glu Ile Gly Glu Thr Glu
    1200                1205                1210

GGA AAG TTT ATT GTA GAT AGC GTG GAA CTA CTC CTC ATG GAA
Gly Lys Phe Ile Val Asp Ser Val Glu Leu Leu Leu Met Glu
1215                1220                1225

GAA TAGGATCATA           3763
                                            Glu
                                             123

CAAGTATAGC AGTTTAATAA ATATTAATTA AAATAGTAGT CTAACTTCCG TTCCAATTAA    3823

ATAAGTAAAT TACAGTTGTA AAAAGAAAAC GGACATCACT CTTCAGAGAG CGATGTCCGT    3883

TTTTTATATG GTGTGTGCTA ATGATAAATG TGCACGAAAT TATATTGTCA A             3934
```

( 2 ) INFORMATION FOR SEQ ID NO:4:

( i ) SEQUENCE CHARACTERISTICS:
        ( A ) LENGTH: 1229 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Leu Thr Ser Asn Arg Lys Asn Glu Asn Glu Ile Ile Asn Ala Leu Ser
 1               5                  10                  15

Ile Pro Thr Val Ser Asn Pro Ser Thr Gln Met Asn Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60
```

```
Arg Ile Leu Gly Val Leu Gly Val Pro Phe Ala Gly Gln Leu Ala Ser
 65                  70                  75                  80

Phe Tyr Ser Phe Leu Val Gly Glu Leu Trp Pro Ser Gly Arg Asp Pro
                 85                  90                  95

Trp Glu Ile Phe Leu Glu His Val Gln Leu Ile Arg Gln Gln Val
            100                 105                 110

Thr Glu Asn Thr Arg Asn Thr Ala Ile Ala Arg Leu Glu Gly Leu Gly
            115                 120                 125

Arg Gly Tyr Arg Ser Tyr Gln Gln Ala Leu Glu Thr Trp Leu Asp Asn
        130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ala Ser Ser Asp Val Asn Gln Tyr Tyr Gln Glu Gln Ile Arg Tyr Thr
210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
            275                 280                 285

Arg Glu Ile Tyr Thr Asp Pro Ile Gly Arg Thr Asn Ala Pro Ser Gly
        290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr Gln Gly Leu Thr Asn Asn Thr Ser Ile Asn
    370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495
```

```
Thr  Asn  Thr  Ile  Gly  Pro  Asn  Arg  Ile  Thr  Gln  Ile  Pro  Leu  Val  Lys
               500                      505                     510

Ala  Leu  Asn  Leu  His  Ser  Gly  Val  Thr  Val  Val  Gly  Gly  Pro  Gly  Phe
          515                      520                     525

Thr  Gly  Gly  Asp  Ile  Leu  Arg  Arg  Thr  Asn  Thr  Gly  Thr  Phe  Gly  Asp
     530                      535                     540

Ile  Arg  Leu  Asn  Ile  Asn  Val  Pro  Leu  Ser  Gln  Arg  Tyr  Arg  Val  Arg
545                      550                     555                     560

Ile  Arg  Tyr  Ala  Ser  Thr  Thr  Asp  Leu  Gln  Phe  Phe  Thr  Arg  Ile  Asn
                565                     570                     575

Gly  Thr  Thr  Val  Asn  Ile  Gly  Asn  Phe  Ser  Arg  Thr  Met  Asn  Arg  Gly
               580                      585                     590

Asp  Asn  Leu  Glu  Tyr  Arg  Ser  Phe  Arg  Thr  Ala  Gly  Phe  Ser  Thr  Pro
          595                      600                     605

Phe  Asn  Phe  Leu  Asn  Ala  Gln  Ser  Thr  Phe  Thr  Leu  Gly  Ala  Gln  Ser
     610                      615                     620

Phe  Ser  Asn  Gln  Glu  Val  Tyr  Ile  Asp  Arg  Val  Glu  Phe  Val  Pro  Ala
625                      630                     635                     640

Glu  Val  Thr  Phe  Glu  Ala  Glu  Tyr  Asp  Leu  Glu  Arg  Ala  Gln  Lys  Ala
               645                      650                     655

Val  Asn  Ala  Leu  Phe  Thr  Ser  Thr  Asn  Pro  Arg  Arg  Leu  Lys  Thr  Asp
          660                      665                     670

Val  Thr  Asp  Tyr  His  Ile  Asp  Gln  Val  Ser  Asn  Met  Val  Ala  Cys  Leu
          675                      680                     685

Ser  Asp  Glu  Phe  Cys  Leu  Asp  Glu  Lys  Arg  Glu  Leu  Phe  Glu  Lys  Val
          690                      695                     700

Lys  Tyr  Ala  Lys  Arg  Leu  Ser  Asp  Glu  Arg  Asn  Leu  Leu  Gln  Asp  Pro
705                      710                     715                     720

Asn  Phe  Thr  Phe  Ile  Ser  Gly  Gln  Leu  Ser  Phe  Ala  Ser  Ile  Asp  Gly
               725                      730                     735

Gln  Ser  Asn  Phe  Pro  Ser  Ile  Asn  Glu  Leu  Ser  Glu  His  Gly  Trp  Trp
          740                      745                     750

Gly  Ser  Ala  Asn  Val  Thr  Ile  Gln  Glu  Gly  Asn  Asp  Val  Phe  Lys  Glu
          755                      760                     765

Asn  Tyr  Val  Thr  Leu  Pro  Gly  Thr  Phe  Asn  Glu  Cys  Tyr  Pro  Asn  Tyr
770                      775                     780

Leu  Tyr  Gln  Lys  Ile  Gly  Glu  Ser  Glu  Leu  Lys  Ala  Tyr  Thr  Arg  Tyr
785                      790                     795                     800

Gln  Leu  Arg  Gly  Tyr  Ile  Glu  Asp  Ser  Gln  Asp  Leu  Glu  Ile  Tyr  Leu
               805                      810                     815

Ile  Arg  Tyr  Asn  Ala  Lys  His  Glu  Thr  Leu  Asp  Val  Pro  Gly  Thr  Asp
               820                      825                     830

Ser  Leu  Trp  Pro  Leu  Ser  Val  Glu  Ser  Pro  Ile  Gly  Arg  Cys  Gly  Glu
          835                      840                     845

Pro  Asn  Arg  Cys  Ala  Pro  His  Phe  Glu  Trp  Asn  Pro  Asp  Leu  Asp  Cys
     850                      855                     860

Ser  Cys  Arg  Asp  Gly  Glu  Arg  Cys  Ala  His  His  Ser  His  His  Phe  Thr
865                      870                     875                     880

Leu  Asp  Ile  Asp  Val  Gly  Cys  Thr  Asp  Leu  His  Glu  Asn  Leu  Gly  Val
               885                      890                     895

Trp  Val  Val  Phe  Lys  Ile  Lys  Thr  Gln  Glu  Gly  Tyr  Ala  Arg  Leu  Gly
               900                      905                     910

Asn  Leu  Glu  Phe  Ile  Glu  Glu  Lys  Pro  Leu  Ile  Gly  Glu  Ala  Leu  Ser
```

```
                        915                           920                            925
   Arg   Val   Lys   Arg   Ala   Glu   Lys   Trp   Arg   Asp   Lys   Arg   Glu   Lys   Leu
               930                           935                     940

Gln   Leu   Glu   Thr   Lys   Arg   Val   Tyr   Thr   Glu   Ala   Lys   Glu   Ala   Val   Asp
   945                           950                           955                           960

Ala   Leu   Phe   Val   Asp   Ser   Gln   Tyr   Asp   Gln   Leu   Gln   Ala   Asp   Thr   Asn
                           965                           970                           975

Ile   Gly   Met   Ile   His   Ala   Ala   Asp   Lys   Leu   Val   His   Arg   Ile   Arg   Glu
                     980                           985                           990

Ala   Tyr   Leu   Ser   Glu   Leu   Pro   Val   Ile   Pro   Gly   Val   Asn   Ala   Glu   Ile
               995                           1000                          1005

Phe   Glu   Glu   Leu   Glu   Gly   His   Ile   Ile   Thr   Ala   Met   Ser   Leu   Tyr   Asp
               1010                          1015                          1020

Ala   Arg   Asn   Val   Val   Lys   Asn   Gly   Asp   Phe   Asn   Asn   Gly   Leu   Thr   Cys
   1025                          1030                          1035                          1040

Trp   Asn   Val   Lys   Gly   His   Val   Asp   Val   Gln   Ser   His   His   Arg   Ser
                           1045                          1050                          1055

Asp   Leu   Val   Ile   Pro   Glu   Trp   Glu   Ala   Glu   Val   Ser   Gln   Ala   Val   Arg
                     1060                          1065                          1070

Val   Cys   Pro   Gly   Arg   Gly   Tyr   Ile   Leu   Arg   Val   Thr   Ala   Tyr   Lys   Glu
               1075                          1080                          1085

Gly   Tyr   Gly   Glu   Gly   Cys   Val   Thr   Ile   His   Glu   Ile   Glu   Asn   Asn   Thr
               1090                          1095                          1100

Asp   Glu   Leu   Lys   Phe   Lys   Asn   Cys   Glu   Glu   Glu   Glu   Val   Tyr   Pro   Thr
   1105                          1110                          1115                          1120

Asp   Thr   Gly   Thr   Cys   Asn   Asp   Tyr   Thr   Ala   His   Gln   Gly   Thr   Ala   Ala
                           1125                          1130                          1135

Cys   Asn   Ser   Arg   Asn   Ala   Gly   Tyr   Glu   Asp   Ala   Tyr   Glu   Val   Asp   Thr
                     1140                          1145                          1150

Thr   Ala   Ser   Val   Asn   Tyr   Lys   Pro   Thr   Tyr   Glu   Glu   Glu   Thr   Tyr   Thr
                     1155                          1160                          1165

Asp   Val   Arg   Arg   Asp   Asn   His   Cys   Glu   Tyr   Asp   Arg   Gly   Tyr   Val   Asn
               1170                          1175                          1180

Tyr   Pro   Pro   Val   Pro   Ala   Gly   Tyr   Val   Thr   Lys   Glu   Leu   Glu   Tyr   Phe
   1185                          1190                          1195                          1200

Pro   Glu   Thr   Asp   Thr   Val   Trp   Ile   Glu   Ile   Gly   Glu   Thr   Glu   Gly   Lys
                           1205                          1210                          1215

Phe   Ile   Val   Asp   Ser   Val   Glu   Leu   Leu   Leu   Met   Glu   Glu
                     1220                          1225
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: circular ( i i ) MOLECULE TYPE: DNA (genomic)

( x i ) SEQUENCE DESCRIPTION: SEQ ID NO:5:

AAGTTTCGCA TCCATCGATG          20